United States Patent
Wakai et al.

(10) Patent No.: US 8,447,090 B2
(45) Date of Patent: *May 21, 2013

(54) MEDICAL IMAGE PROCESSING APPARATUS AND MEDICAL IMAGE DIAGNOSIS APPARATUS

(75) Inventors: Satoshi Wakai, Nasushiobara (JP); Hitoshi Yamagata, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/408,527

(22) Filed: Feb. 29, 2012

(65) Prior Publication Data
US 2012/0207371 A1  Aug. 16, 2012

Related U.S. Application Data

(62) Division of application No. 12/167,561, filed on Jul. 3, 2008, now Pat. No. 8,213,699.

(30) Foreign Application Priority Data
Jul. 5, 2007 (JP) ................................. 2007-177637

(51) Int. Cl.
*G06K 9/00* (2006.01)
(52) U.S. Cl.
USPC ........................................................ 382/131

(58) Field of Classification Search
USPC ............ 382/128, 130–132; 378/62, 63, 98.12
See application file for complete search history.

(56) References Cited

U.S. PATENT DOCUMENTS

| | | | |
|---|---|---|---|
| 6,795,571 B2 | 9/2004 | Kusch | |
| 6,937,750 B2 | 8/2005 | Natanzon et al. | |
| 8,213,699 B2 * | 7/2012 | Wakai et al. | 382/131 |
| 2005/0008209 A1 | 1/2005 | Matsumoto | |
| 2006/0004275 A1 | 1/2006 | Vija et al. | |
| 2006/0239524 A1 | 10/2006 | Desh et al. | |

FOREIGN PATENT DOCUMENTS

| | | |
|---|---|---|
| JP | 10-127623 | 5/1998 |
| JP | 2003-153877 | 5/2003 |
| JP | 2003-517361 A | 5/2003 |

OTHER PUBLICATIONS

Office Action issued Dec. 11, 2012 in Japanese Patent Application No. 2008-153251.

* cited by examiner

*Primary Examiner* — Jurie Yun
(74) *Attorney, Agent, or Firm* — Oblon, Spivak, McClelland, Maier & Neustadt, L.L.P.

(57) ABSTRACT

A medical image processing apparatus comprises: an acquiring part configured to acquire a morphological image that is formed by a first apparatus and shows the morphology of an organ of an object, and a functional image that is formed by a second apparatus different from the first apparatus and shows the state of the organ; a display; and a processor configured to cause the display to display a synthetic image based on the morphological image and the functional image.

8 Claims, 17 Drawing Sheets

MEDICAL IMAGE PROCESSING APPARATUS AND MEDICAL IMAGE DIAGNOSIS APPARATUS

CROSS-REFERENCE TO RELATED APPLICATIONS

The present application is a divisional of U.S. application Ser. No. 12/167,561 filed on Jul. 3, 2008, and claims priority to JP 2007-177637 filed on Jul. 5, 2007, the entire contents of each of which are incorporated herein by reference.

BACKGROUND OF THE INVENTION

1. Field of the Invention

The present invention relates to a medical image processing apparatus and a medical image diagnosis apparatus, and specifically relates to a technology of displaying by synthesizing a morphological image and a functional image of an object.

2. Description of the Related Art

In recent years, the propagation of medical image diagnosis apparatuses for acquiring images representing the morphology or the function of an object has been promoted. Medical image diagnosis apparatuses include the X-ray diagnosis apparatus, X-ray CT (Computed Tomography) apparatus, MRI (Magnetic Resonance Imaging) apparatus, ultrasound diagnosis apparatus, and nuclear medical diagnosis apparatus.

Ischemic heart disease is one of diseases in which the effectiveness of a medical image diagnosis apparatus is demonstrated. Ischemic heart disease is a disease in which constriction is caused in a coronary artery due to the effects of arteriosclerosis, thrombus, etc., resulting in a lack of oxygen supply or nutrients supply to the cardiac muscle.

A method of measuring the constriction rate of blood vessels by referring to images (morphological images) representing the morphology of the heart of an object has been widely used for the conventional diagnosis or treatment of ischemic heart disease. However, it is known that the correlation between blood vessels having developed arteriosclerosis or the like (culprit coronary artery) and the constriction rate is, in general, not particularly high. Therefore, it is not easy to diagnose or treat with high accuracy by referring to only the constriction rate.

Further, it is also possible to think of making a diagnosis by referring to images representing the function of the heart of an object (functional images). However, it is not possible to accurately specify the position of a culprit coronary artery from only functional images. Therefore, diagnosis and treatment with accuracy is difficult.

In view of such a situation, a technology of displaying by synthesizing a morphological image and a functional image has been developed. Such an image acquired by synthesizing a plurality of images (may be morphological images only or functional images only) is referred to as a fusion image or the like.

Technologies that make it possible to display a fusion image have been disclosed in Japanese Unexamined Patent Application Publication JP-A 10-127623 and Japanese Unexamined Patent Application Publication JP-A 2003-153877. The technology described in JP-A 10-127623 is to display by creating a fusion image obtained by synthesizing a tomographic image acquired by an X-ray CT apparatus and a bloodstream distribution image acquired by an ultrasound diagnosis apparatus. The technology described in JP-A 2003-153877 is to display by creating a fusion image obtained by synthesizing a morphological image acquired by an MRI apparatus and a bloodstream distribution image acquired by an ultrasound diagnosis apparatus.

However, in the conventional techniques mentioned above, it is difficult to diagnose or treat with favorable accuracy for the following reasons.

First, in the case of referring to only morphological images or only functional images, there is a problem of the accuracy of the diagnosis as mentioned above. In particular, in the case of referring to morphological images, there is a risk of overlooking constricted sites in the images.

Furthermore, as another method, it is known to obtain the difference between a normal morphological image and a morphological image (contrast enhanced image) taken by administering a contrast agent to extract an image of a blood vessel and display (referred to as, e.g., digital subtraction angiography). However, this method is generally regarded as improper to examinations of a heart, which has an intricate blood vessel system.

Moreover, in the case of referring to a fusion image stated in JP-A 10-127623 and in JP-A 2003-153877, only bloodstream distribution images can be acquired as functional images, so it is difficult to accurately specify the position of a culprit coronary artery, and thus, it is difficult to diagnose or treat with accuracy.

In addition, in conventional techniques, it is necessary to perform an examination for specifying the position of a culprit coronary artery and a treatment based on the result thereof. However, it is necessary to execute a catheter examination in both the processes, and there is a problem of significant stress being imposed on an object. Furthermore, there is also a problem in that the object is subjected to radiation poisoning in both the processes. Moreover, there is also a problem of having a long interval between the examination and the treatment (e.g., approx. two weeks).

SUMMARY OF THE INVENTION

The present invention has been devised to solve the problems as described above, and an object of the present invention is to provide a medical image processing apparatus and a medical image diagnosis apparatus that make it possible to diagnose or treat an organ such as a heart with accuracy.

The present invention has been devised to solve the problems as described above, and an object of the present invention is to provide a medical image processing apparatus and a medical image diagnosis apparatus that make it possible to diagnose or treat an organ such as a heart with accuracy.

In a first aspect of the present invention, a medical image processing apparatus comprises: an acquiring part configured to acquire a morphological image formed by a first apparatus and representing a morphology of an organ of an object and a functional image formed by a second apparatus different from the first apparatus and representing a state of the organ; a display; and a processor configured to cause the display to display a synthetic image based on the morphological image and the functional image.

In the first aspect, the apparatus acts so as to acquire the morphological image and the functional image of an organ formed by separate apparatuses, respectively, and display a synthetic image based on these images. According to the first aspect, it is possible to observe the morphology of the organ in detail with the morphological image, and it is also possible to grasp the state of the organ in detail by referring to the functional image. Furthermore, since it is possible to display by synthesizing the morphological image and the functional image, it is possible to highly accurately grasp a site functioning favorably and a site functioning unfavorably in the heart. Therefore, according to the first aspect, it is possible to increase the accuracy of the diagnosis or treatment of the organ.

In a second aspect of the present invention, a medical image processing apparatus comprises: an acquiring part configured to acquire a morphological image showing a morphology of a heart of an object and a functional image showing a state of wall motion of the heart; a display; and a processor configured to cause the display to display a synthetic image based on the morphological image and the functional image, specify a culprit coronary artery region in the synthetic image based on the functional image, and cause to display information indicating the specified culprit coronary artery region together with the synthetic image.

In the second aspect, the apparatus acquires the morphological image of the heart and the functional image showing the state of wall motion, and displays a synthetic image based on these images. Furthermore, in the second aspect, the apparatus specifies the culprit coronary artery region within the synthetic image based on the functional image, and displays the information indicating the specified culprit coronary artery region together with the synthetic image. According to the second aspect, it is possible to increase the accuracy of the diagnosis or treatment of the heart, and it is also possible to increase the efficiency and save labor in an operation of specifying the culprit coronary artery.

In a third aspect of the present invention, a medical image diagnosis apparatus comprises: a morphological-image forming part configured to detect data in which a morphology of the inside of an object is incorporated and form a morphological image showing a morphology of a range including an organ of the object based on the detected data; a part configured to receive a functional image formed by another medical image diagnosis apparatus and representing a state of the organ; a display; and a processor configured to cause the display to display a synthetic image based on the morphological image and the functional image.

In the third aspect, the apparatus acts so as to form the morphological image of the organ by detecting the data in which the morphology of the inside of the object body is incorporated, receive the functional image showing the state of the organ from outside, and display the synthetic image based on the morphological image and the functional image. According to the third aspect, it is possible to increase the accuracy of the diagnosis or treatment of the organ.

In a fourth aspect of the present invention, a medical image diagnosis apparatus comprises: a part configured to receive a morphological image formed by another medical image diagnosis apparatus and representing a morphology of a range including an organ of an object; a part configured to detect data in which a function or morphology of the organ is incorporated and form a functional image showing a state of the organ based on the detected data; a display; and a processor configured to cause the display to display a synthetic image based on the morphological image and the functional image.

In the fourth aspect, the apparatus acts so as to receive the morphological image of the organ from outside, form the functional image by detecting the data in which the function or the morphology of the organ is incorporated, and display the synthetic image based on the morphological image and the functional image. According to the fourth aspect, it is possible to increase the accuracy of the diagnosis or treatment of the organ.

In a fifth aspect of the present invention, a medical image diagnosis apparatus comprises: a morphological-image forming part configured to detect data in which a morphology of the inside of an object is incorporated and form a morphological image showing a morphology of a range including a heart of the object based on the detected data; a part configured to receive a functional image formed by another medical image diagnosis apparatus and representing a state of wall motion of the heart; a display; and a processor configured to cause the display to display a synthetic image based on the morphological image and the functional image, specify a culprit coronary artery region in the synthetic image based on the functional image, and display information indicating the specified culprit coronary artery region together with the synthetic image.

In the fifth aspect, the apparatus forms the morphological image of the organ by detecting the data in which the morphology of the inside of the object body is incorporated, receives the functional image showing the state of wall motion of the heart from outside, and displays the synthetic image based on the morphological image and the functional image. Furthermore, in the fifth aspect, the apparatus specifies the culprit coronary artery region within the synthetic image based on the functional image, and displays the information indicating the specified culprit coronary artery region together with the synthetic image. According to the fifth aspect, it is possible to increase the accuracy of the diagnosis or treatment of the organ, and it is also possible to increase the efficiency and save labor in an operation of specifying the culprit coronary artery.

In a sixth aspect of the present invention, a medical image diagnosis apparatus comprises: a part configured to receive a morphological image formed by another medical image diagnosis apparatus and representing a morphology of a range including a heart of an object; a part configured to detect data indicating a function or morphology of the heart and form a functional image showing a state of wall motion of the heart based on the detected data; a display; and a processor configured to cause the display to display a synthetic image based on the morphological image and the functional image, specify a culprit coronary artery region in the synthetic image based on the functional image, and cause to display information indicating the specified culprit coronary artery region together with the synthetic image.

In the sixth aspect, the apparatus receives the morphological image of the heart from outside, forms the functional image showing the state of wall motion of the heart by detecting the data indicating the function or the morphology of the heart, and displays the synthetic image based on the morphological image and the functional image. Furthermore, in the sixth aspect, the apparatus specifies the culprit coronary artery region within the synthetic image based on the functional image, and displays the information indicating the specified culprit coronary artery region together with the synthetic image. According to the sixth aspect, it is possible to increase the accuracy of the diagnosis or treatment of the organ, and it is also possible to increase the efficiency and save labor in an operation of specifying the culprit coronary artery.

DETAILED DESCRIPTION OF THE PREFERRED EMBODIMENTS

An embodiment of the medical image processing apparatus and the medical image diagnosis apparatus according to the present invention will be described in detail with reference to the drawings. Below, first to fourth embodiments of the medical image processing apparatus according to the present invention will be described, and thereafter, an embodiment of the medical image diagnosis apparatus according to the present invention will be described.

First Embodiment

The medical image processing apparatus according to the first embodiment realizes highly accurate diagnosis and treatment by acquiring a morphological image showing the morphology of a heart and a functional image showing the state of wall motion of the heart to display a synthetic image thereof.

Figure 1:
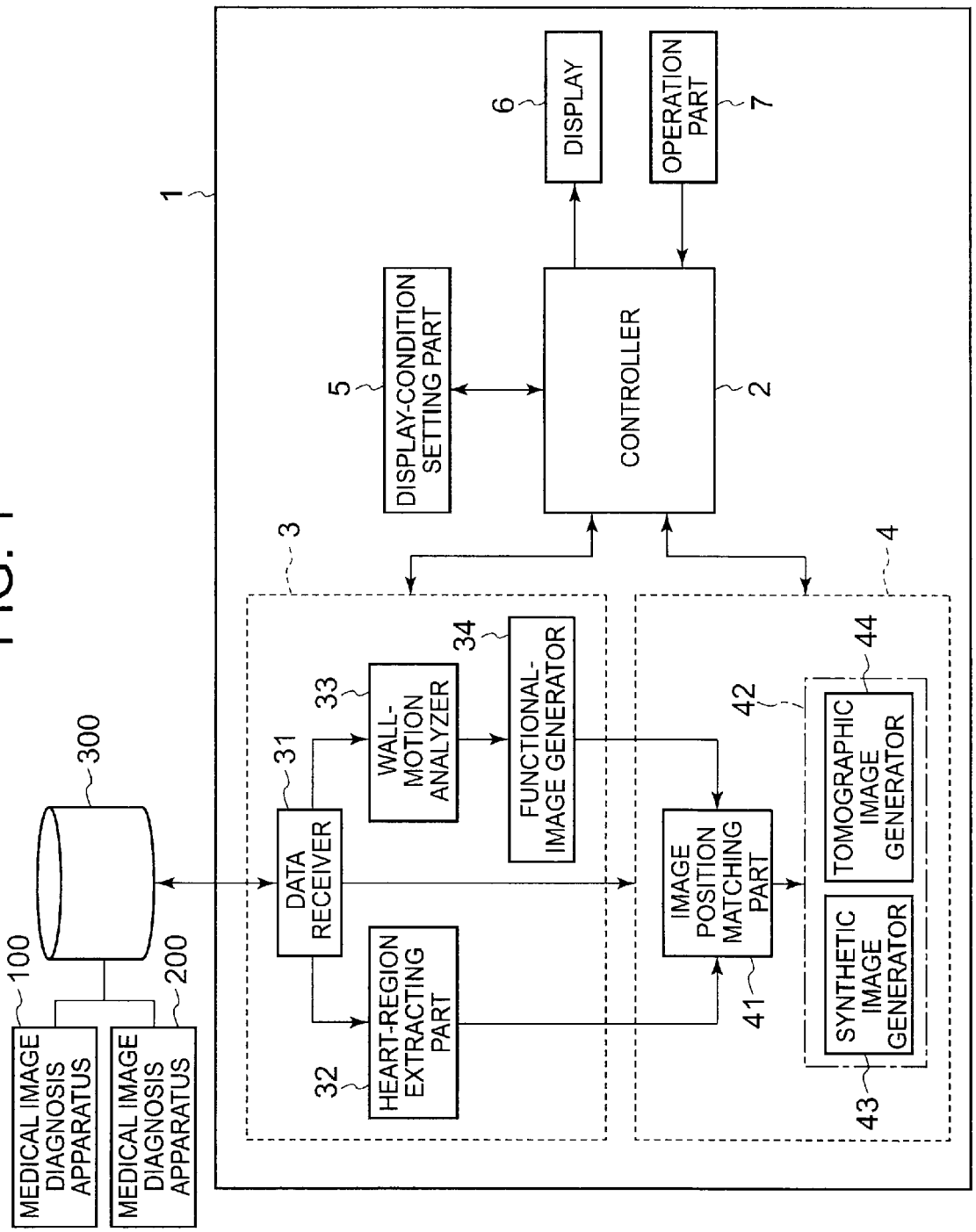
FIG. 1 is a schematic block diagram representing one example of the configuration of a first embodiment of a medical image processing apparatus according to the present invention.

FIG. 1 shows an example of the configuration of the medical image processing apparatus according to the present embodiment. The medical image processing apparatus 1 shown in FIG. 1 is connected to a medical image database 300 via a communication line such as a LAN (Local Area Network).

The medical image database 300 stores and manages medical information such as medical images acquired by various types of medical image diagnosis apparatuses. The medical image database 300 includes a large-capacity storage device such as a hard disk drive and a computer program for managing the medical information stored in the storage device.

The medical image database 300 includes, for example, PACS (Picture Archiving and Communication System). Otherwise, it may include a medical information system such as RIS (Radiology Information System) and HIS (Hospital Information System).

The medical image database 300 is connected to various types of medical image diagnosis apparatuses via communication lines. In this embodiment, the medical image database 300 is connected to a medical image diagnosis apparatus 100 and a medical image diagnosis apparatus 200.

The medical image diagnosis apparatus 100 forms an image that shows the morphology of the inside of an object body. To be specific, the medical image diagnosis apparatus 100 detects data in which the morphology of the inside of the object is incorporated, and forms a morphological image of a range including the heart of the object based on the data. The medical image diagnosis apparatus 100 forms a still image and a moving image of the range including the heart.

The medical image diagnosis apparatus 100 is composed of any medical image diagnosis apparatus capable of acquiring a morphological image of an object, such as an X-ray diagnosis apparatus, an X-ray CT apparatus, an MRI apparatus, an ultrasound diagnosis apparatus and a nuclear medical diagnosis apparatus.

The medical image diagnosis apparatus 200 forms an image provided for examination of the function of the inside of the object body (a functional image). To be specific, the medical image diagnosis apparatus 200 forms an image provided for analysis of wall motion of the heart of the object. The medical image diagnosis apparatus 200 forms, for example, a moving image of a range including the heart of the object.

The medical image diagnosis apparatus 200 is composed of, for example, an apparatus such as an X-ray diagnosis apparatus, an X-ray CT apparatus, an MRI apparatus, an ultrasound diagnosis apparatus and a nuclear medical diagnosis apparatus (PET, SPECT, etc.), and forms an image provided for analysis of the wall motion of a heart. In general, the wall motion analysis of a heart is conducted by an ultrasound diagnosis apparatus, an MRI apparatus, a myocardial SPECT (single photon emission computed tomography), a myocardial PET (positron emission tomography), etc. In particular, as functional images representing the state of wall motion, images (ultrasound images) acquired by an ultrasound diagnosis apparatus are generally used. In the case of using an ultrasound diagnosis apparatus, it is also possible to form, for example, functional images such as Doppler images.

The number of the medical image diagnosis apparatuses is not limited to two. For example, it is possible to configure to form morphological images and functional images by using three or more medical image diagnosis apparatuses. Otherwise, it is possible to configure to form both morphological images and functional images by using a single medical image diagnosis apparatus.

The respective medical image diagnosis apparatuses 100 and 200 transmit (image data of) formed images to the medical image database 300. At this moment, information such as object information and examination information is attached to each of the images.

The object information is information on an object (a patient). The object information includes, for example, the ID, name, gender, age, etc. of the patient.

The examination information is information on an examination using the medical image diagnosis apparatus. The examination information includes, for example, examination date/time, imaging conditions, body-position information indicating the orientation (the direction of the head, the direction of the lower limb, etc.) of the object in images, and the like. Furthermore, in a case where electrocardiogram gated radiography for acquiring images in synchronism with heart beats is conducted, electrocardiogram synchronous information indicating the phase of the heart corresponding to each image is included in the examination information.

These information are attached to images as, for example, DICOM patient demographic data (also referred to as incidental information). The DICOM (Digital Imaging and Communications in Medicine) is standard in the digital medical image field.

Moreover, in a case where both a morphological image and a functional image of the object (particularly, the heart) have already been acquired and the positions of these images have already been matched, the medical image database 300 can store the parameter acquired in the position matching.

The positions of images are matched through coordinate transformation of associating a coordinate system in which a morphological image is defined (first coordinate system) and a coordinate system in which a functional image is defined (second coordinate system). The coordinate transformation parameter is given as, for example, a transformation matrix for expressing the coordinate transformation.

As a specific example, in a case where both the morphological image and the functional image are three-dimensional images, a 3×3 matrix, which associates a first three-dimensional coordinate system in which the volume data of the morphological image is defined with a second three-dimensional coordinate system in which the volume data of the functional image is defined, is applied as the coordinate transformation parameter.

The positions of images can be matched by employing any publicly known technology, such as a method of matching the positions of landmarks in respective images and a method using the correlation coefficient of images.

The medical image database 300 stores and manages images and incidental information that have been transmitted from the medical image diagnosis apparatuses 100 and 200. The medical image database 300 receives a request from the apparatus on the communication lines, such as the medical image processing apparatus 1, searches images, etc., and transmits to the apparatus of the source of the request.

[Medical Image Processing Apparatus]

The medical image processing apparatus 1 will now be described. The medical image processing apparatus 1 receives images supplied from the medical image database 300, and generates and displays a synthetic image of a morphological image and a functional image.

The medical image processing apparatus 1 has a similar configuration as to that of a generally-used computer. That is, the medical image processing apparatus 1 comprises a microprocessor such as a CPU, a RAM, a ROM, a hard disk drive, a communication interface (a LAN card etc.), a display device (an LCD, a CRT, etc.), and an operation device (a keyboard, a mouse, etc.).

A storage device such as a hard disk drive previously stores computer programs for making the medical image processing apparatus 1 execute an operation characteristic to the embodiment, and various types of information.

As shown in FIG. 1, the medical image processing apparatus 1 comprises a controller 2, a data-acquiring part 3, a data processor 4, a display-condition setting part 5, a display 6, and an operation part 7.

The controller 2 controls each part of the medical image processing apparatus 1. The controller 2 includes a microprocessor, a RAM, a ROM, a hard disk drive, etc., that operate based on the abovementioned computer programs.

The data-acquiring part 3 executes various types of processing for acquiring morphological images representing the morphology of a heart and functional images representing the state of wall motion of the heart. The data-acquiring part 3 is one example of the "acquiring part" according to the present invention.

The data-acquiring part 3 is provided with a data receiver 31, a heart-region extracting part 32, a wall-motion analyzer 33 and a functional-image generator 34.

The data receiver 31 communicates with the medical image database 300 via communication lines and receives medical images, incidental information, etc.

Describing in detail, the data receiver 31 is controlled by the controller 2 to transmit a data transmission request to the medical image database 300. The data transmission request includes information such as the patient ID, examination date/time, and network address of the request source (medical image processing apparatus 1).

The medical image database 300 searches data to be transmitted, based on the patient ID, examination date/time, etc., and transmits the searched-out data to the medical image processing apparatus 1 based on the network address. The data receiver 31 receives the data transmitted from the medical image database 300. The received data is stored in a storage device such as a hard disk drive.

The data receiver 31 includes a microprocessor, a RAM, a ROM, a hard disk drive, a communication interface, etc. The data receiver 31 is one example of the "receiver" according to the present invention.

When receiving an image of a range including a heart, the data receiver 31 transmits the image to the heart-region extracting part 32. The heart-region extracting part 32, for example, executes threshold processing with respect to the pixel values of pixels forming the image, and extracts an image region corresponding to the heart (a heart region). The threshold value is previously stored in the hard disk drive or the like. The heart-region extracting part 32 specifically extracts the heart region from a three-dimensional image (volume data).

Instead of automatically extracting the heart region as described above, it is also possible to configure so that an operator designates the heart region. In this case, first, an image is displayed on the display 6. In a case where the image is a three-dimensional image, the volume data is subjected to rendering and a pseudo three-dimensional image is displayed. The operator designates a heart region within the displayed image by, for example, a dragging operation with a mouse. The heart-region extracting part 32 extracts the designated region from the image.

The process of extracting the heart region is not limited to the above, and it is also possible to apply any publicly known technology. The heart-region extracting part 32 transmits the extracted heart region to an image position matching part 41. The heart-region extracting part 32 includes a microprocessor, a RAM, a ROM, a hard disk drive, etc. The heart-region extracting part 32 is one example of the "heart-region extracting part" according to the present invention.

The wall-motion analyzer 33 will now be described. The data receiver 31 transmits an image provided for analysis of wall motion of a heart to the wall-motion analyzer 33. Such an image includes a moving image of a heart acquired by the ultrasound diagnosis apparatus.

The wall-motion analyzer 33 acquires the state of the wall motion of a heart (e.g., a displacement amount, a displacement direction, a displacement speed), by tracking the movement of each position of the heart wall with respect to a plurality of frames forming a moving image. Such wall motion analysis can be performed by employing any conventional method. The wall-motion analyzer 33 transmits the result of analysis of wall motion to the functional-image generator 34.

In a case where analysis of wall motion has already been performed by the medical image diagnosis apparatus 200 etc., the wall motion analysis is not required. The wall-motion analyzer 33 includes a microprocessor, a RAM, a ROM, a hard disk drive, etc.

The functional-image generator 34 generates a functional image of a heart based on the result of the analysis of the wall motion acquired by the wall-motion analyzer 33. The functional image is, for example, an image in which the distribution of values of the displacement amount, the displacement speed, etc. showing the state of the wall motion is presented in colors or gradations.

One example is that it is possible to generate a functional image represented by a first color for a site where the displacement amount is greater than a specified value and by a second color for a site where the displacement amount is equal to or more than the specified value. Such an image that is differentiated by color is referred to as a color map or the like. The functional-image generator 34 includes a microprocessor, RAM, ROM, a hard disk drive, etc.

Next, the data processor 4 will now be described. The data processor 4 generates a synthetic image based on a morphological image and a functional image of a heart. The data processor 4 functions together with the controller 2 as one example of the "processor" according to the present invention.

The data processor 4 is provided with an image position matching part 41 and a display image generator 42. Furthermore, the display image generator 42 is provided with a synthetic image generator 43 and a tomographic image generator 44.

The image position matching part 41 executes position matching of a morphological image and a functional image of a heart. The position matching process may be executed in the following manner, for example.

A case where a coordinate transformation parameter between the first coordinate system defining a morphological image and the second coordinate system defining a functional image has already been acquired will be explained. In this case, as described previously, the coordinate transformation parameter is stored in the medical image database 300. The data receiver 31 acquires the coordinate transformation parameter from the medical image database 300, and transmits to the data processor 4.

The image position matching part 41 transforms a coordinate value of the second coordinate system to a coordinate value of the first coordinate system by using the coordinate transformation parameter, and expresses a functional image with the coordinate value of the first coordinate system, thereby defining the morphological image and the functional image by using the same coordinate system (herein, the first coordinate system).

Conversely, it is also possible to process so as to define the morphological image in the second coordinate system. Moreover, it is also possible to define the morphological image and the functional image in a third coordinate system that is transformable with both the first and second coordinate systems.

If both the morphological and the functional image are three-dimensional images, the volume data of both the images are defined in the same three-dimensional coordinate system.

If the coordinate transformation parameter is not stored in the medical image database 300, the image position matching part 41 performs position matching of the morphological image and the functional image by using any publicly known technology as described previously.

The image position matching part 41 transmits the result of the position matching of the morphological image and the functional image to the display image generator 42. The image position matching part 41 includes a microprocessor, a RAM, a ROM, a hard disk drive, etc.

If the position matching of the morphological image and the functional image has already been performed by using a landmark of the heart (basis, apex, papillary muscle, blood vessel, etc.), it is possible to omit the position matching process by the image position matching part 41.

The display image generator 42 generates various types of images displayed in the display 6. The display image generator 42 is provided with the synthetic image generator 43 and the tomographic image generator 44. The display image generator 42 includes a microprocessor, a RAM, a ROM, a hard disk drive, etc.

The synthetic image generator 43 will now be described. A morphological image and a functional image are defined in the same coordinate system by the image position matching part 41. For example, if both the images are three-dimensional images, the volume data of the both are defined in the same three-dimensional coordinate system.

The synthetic image generator 43 generates one image (image data) by synthesizing the morphological image and the functional image thus defined within the same coordinate system. Furthermore, the synthetic image generator 43 properly executes a process of converting the generated image to an image for display.

If both the images are three-dimensional images, the synthetic image generator 43 fuses voxel information (luminance, RGB value, etc.) of the respective voxels of both the images, and expresses both the images in one volume data (synthetic volume data). In other words, the voxel information of the voxels of the morphological image and the voxel information of the voxels of the functional image are allocated in the respective voxels of the synthetic volume data. Therefore, each voxel of the synthetic volume data includes voxel information indicating the morphology and the voxel information indicating the function.

The synthetic image generator 43 generates an image (image data) for display via a rendering process such as volume rendering of the synthetic volume data. The image for display generated in this way is a pseudo three-dimensional image in a state when a heart or the like is viewed from a specified angle of view.

Furthermore, the synthetic image generator 43 sets display colors, gradation, etc., for the image for display.

Instead of the process described above, for example, it is also possible to individually generate the image for display of a morphological image and the image for display of a functional image. In this case, the positions of these images for display are associated with each other by the image position matching part 41. Therefore, it is possible to obtain the same display effects described above by displaying so that one of the images for display is superimposed on the other. At this moment, it is possible to regulate the transparency of the one image displayed on the other image so that the other image can be seen through the one image.

The tomographic image generator 44 will now be described. The tomographic image generator 44 generates tomographic images based on the volume data in a case where a morphological image and a functional image are three-dimensional images. For example, the tomographic image generator 44 generates tomographic images of a heart based on the volume data of a functional image and the synthetic volume data. The process of thus generating tomographic images is executed, for example, by using any publicly known technologies such as MPR (multiplanar reconstruction) and curved MPR (curved MPR). Furthermore, it is also possible to use, as an image for display, a tomographic image (a two-dimensional tomographic image) having been used for formation of a three-dimensional image, as it is. The tomographic image generator 44 is one example of the "tomographic image generator" according to the present invention.

The display-condition setting part 5 will now be described. The display-condition setting part 5 is for setting various types of conditions for displaying images displayed on the display 6. Examples of the display conditions include rendering conditions, geometrical conditions, projection conditions, and the like.

The rendering condition is a condition set in the rendering process for generating a pseudo three-dimensional image from volume data such as volume rendering and MIP (maximum intensity projection). The rendering condition is, for example, the resolution of an image.

The geometrical condition is a condition set with respect to a coordinate system in which an image is defined. The geometrical condition is, for example, a display range and display magnification ratio of an image.

The projection condition is a condition regarding a display mode of a pseudo three-dimensional image. Examples of the projection condition include a projection method (perspective, parallel projection, etc.), angle of view, shift (displacement, direction), and rotation (angle, direction). Furthermore, in the case of displaying two or more images in a superimposed manner, the degree of transparency of the images is also included in the projection conditions.

These display conditions are designated, for example, by the operator. When the operator sets the display condition by using the operation part 7, the controller 2 transmits the content of the setting to the display-condition setting part 5. The display-condition setting part 5 transmits information related to the content of the setting (setting information) to the controller 2. The setting information includes mathematical formulas and various types of data for applying the display condition.

The controller 2 inputs the setting information into the data-acquiring part 3 or the data processor 4. The destination of the input executes processes based on the setting information. For example, the synthetic image generator 43 generates a synthetic image based on the setting information of the geometrical condition. Furthermore, the display image generator 42 sets the display mode of the synthetic image based on the set information of projection conditions.

It is also possible to apply display conditions that have been set by default. Setting information of default display conditions are previously stored in the display-condition setting part 5. In response to a request from the data-acquiring part 3 or data processor 4, for example, the controller 2 acquires information regarding setting of the display conditions from the display-condition setting part 5 and inputs the same in the requested source.

The display 6 is controlled by the controller 2 and displays various types of screens, images, data, etc. The display 6 includes a display device such as an LCD or CRT display. The display 6 is one example of the "display" according to the present invention.

The operation part 7 is operated by the operator to perform operations of the medical image processing apparatus 1, set the display conditions, etc., or input various types of data such as the patient ID, etc. The operation part 7 includes an operation device or an input device such as a mouse or keyboard. The operation part 7 is one example of the "operation part" according to the present invention.

[Operation Mode]

Figure 2:
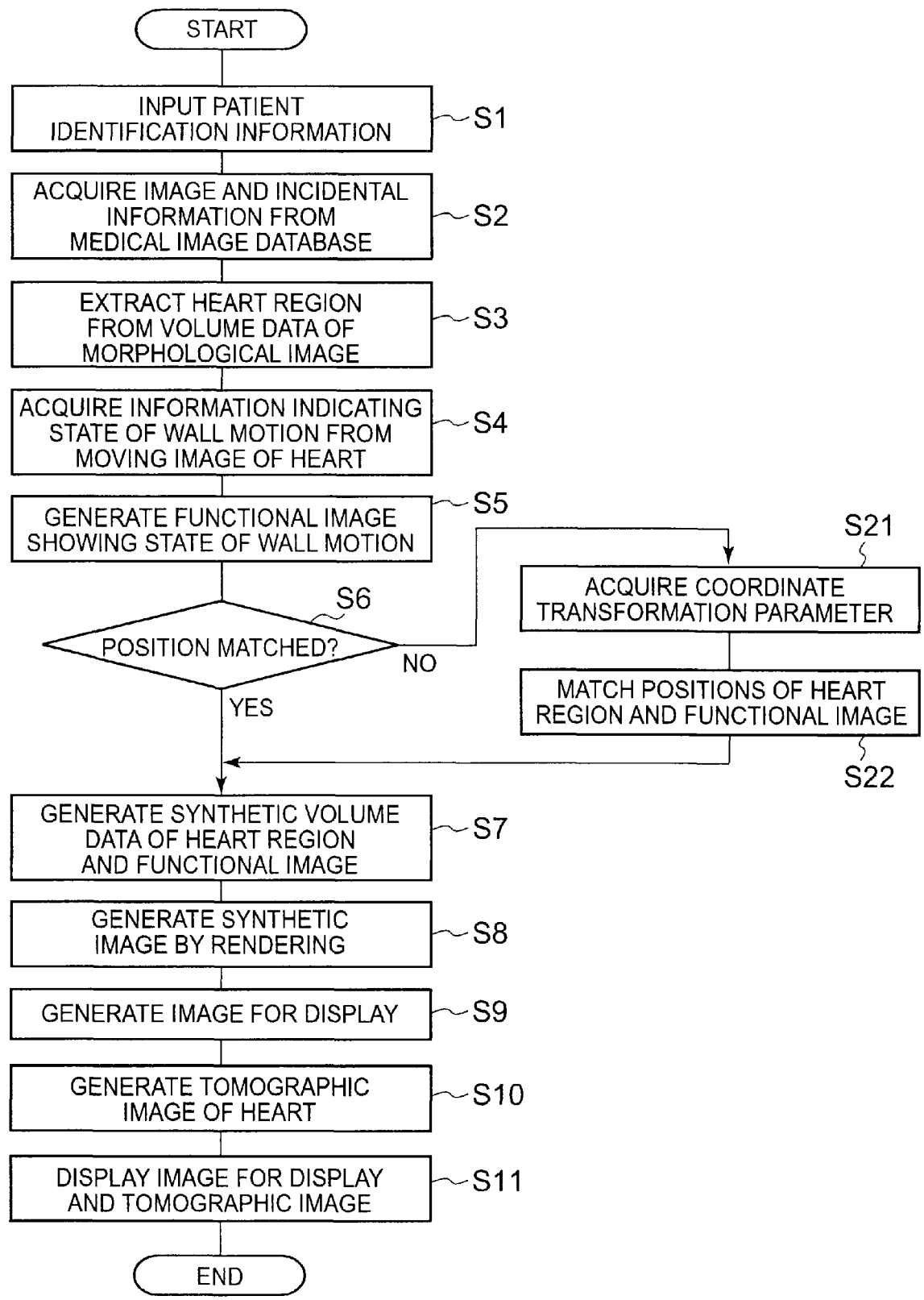
FIG. 2 is a flowchart representing one example of an operation mode of the first embodiment of the medical image processing apparatus according to the present invention.
Figure 3:
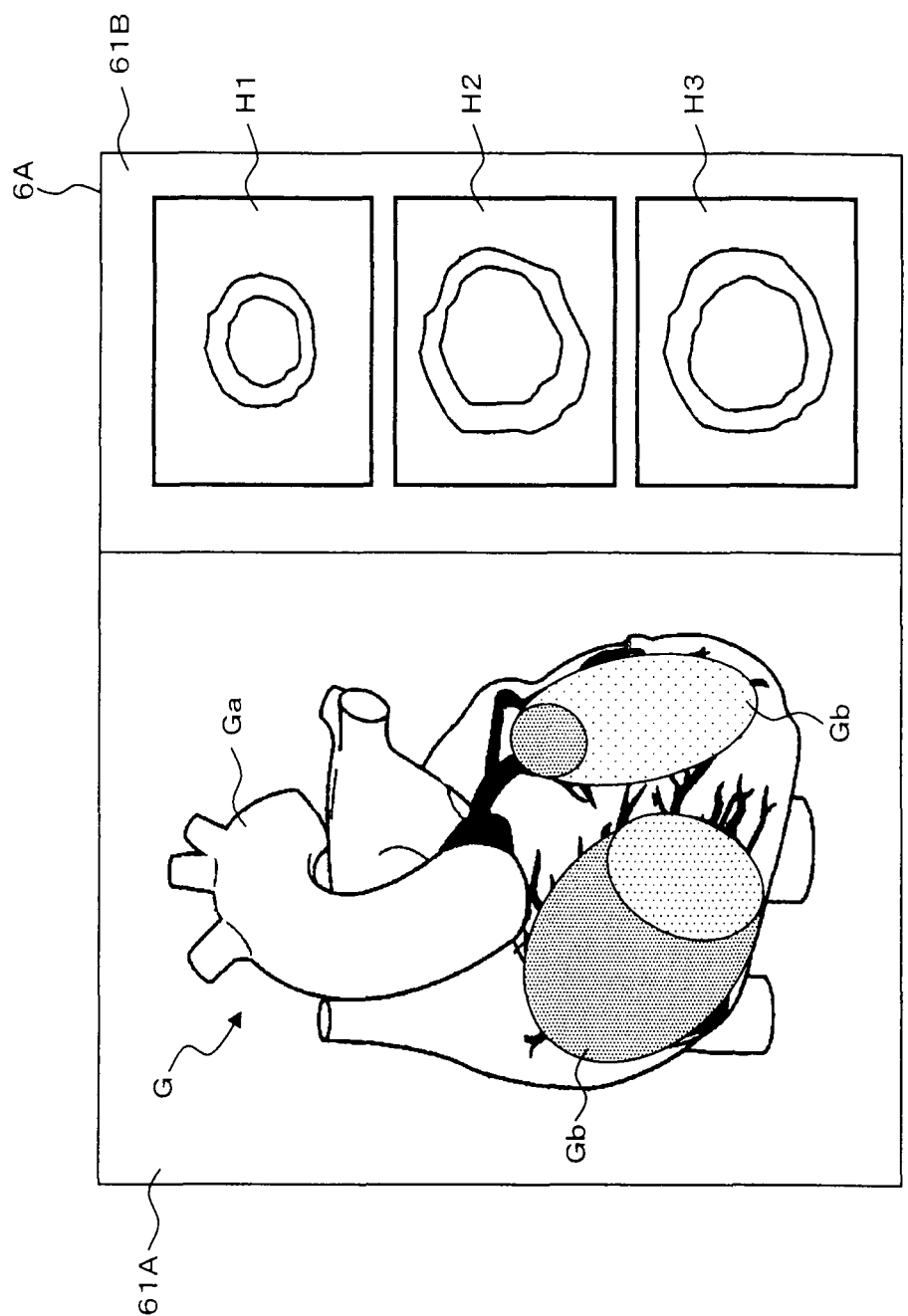
FIG. 3 is a schematic view representing one example of an image displayed in the first embodiment of the medical image processing apparatus according to the present invention.

The operation mode of the medical image processing apparatus 1 will now be described. The flowchart shown in FIG. 2 represents one example of the operation modes of the medical image processing apparatus 1. Furthermore, FIG. 3 shows one example of images to be displayed by the medical image processing apparatus 1.

First, an operator operates the operation part 7 to input patient identification information such as the patient ID (S1). The controller 2 transmits the inputted patient identification information, to the data-acquiring part 3.

The data receiver 31 requests the medical image database 300 to transmit data based on the patient identification information. The medical image database 300 searches the data (morphological image, functional image, incidental information, etc.) based on the request, and transmits the data to the medical image processing apparatus 1. The data receiver 31 receives the data from the medical image database 300 (S2).

In this operation mode, it is assumed that the data receiver 31 has received volume data (and incidental information thereof) of a three-dimensional morphological image of a range that includes the heart of the patient, and a three-dimensional image of the heart (and incidental information thereof). The data receiver 31 inputs the volume data into the heart-region extracting part 32 and inputs a moving image into the wall-motion analyzer 33.

The heart-region extracting part 32 extracts a heart region from the volume data of the morphological image (S3). The heart-region extracting part 32 transmits the extracted heart region to the image position matching part 41.

Furthermore, the wall-motion analyzer 33 acquires information indicating the state of wall motion of the heart (displacement amount, displacement direction, displacement speed, etc.) based on the moving image of the heart (S4). The wall-motion analyzer 33 transmits the acquired information indicating the state of wall motion to the functional-image generator 34.

The functional-image generator 34 generates a functional image showing the state of wall motion based on the information indicating the state of wall motion (S5). The functional-image generator 34 transmits the generated functional image to the image position matching part 41.

Either the steps or the steps 4 and 5 may be performed first. Furthermore, these processes may also be performed in parallel.

The image position matching part 41 determines whether position matching of the heart region extracted in step 3 and the functional image generated in step 5 by landmarks, etc., of the heart has already been performed (S6). This process is performed by, for example, determining whether the position matching of the volume data of the basis of the heart region and the volume data of the basis of the functional image has already been performed.

If it is determined that the position matching has already been performed (S6: Y), the image position matching part 41 transmits the heart region and the functional image to the synthetic image generator 43.

The synthetic image generator 43 synthesizes these images (both are volume data) and generates synthetic volume data (S7). At this moment, the synthetic image generator 43 sets the range, magnification ratio, etc., of the synthetic volume data based on the previously set geometrical conditions. Furthermore, the synthetic image generator 43 performs sampling again by enlarging/reducing the volume data of each image in accordance with the voxel size. At this moment, information of the morphological image (heart region) and information of the functional image are designated to each voxel in a proportional ratio according to the display conditions that have been previously set.

Subsequently, the synthetic image generator 43 generates a three-dimensional synthetic image, which is a pseudo three-dimensional image, by executing a rendering process on the synthetic volume data (S8). This process is executed based on a previously set rendering condition.

Furthermore, the display image generator 42 changes the projection method, angle of view, shift, rotation, etc., of the synthetic image to generate an image for display (S9). This process is executed based on a previously set projection condition. The display image generator 42 transmits the generated image for display to the controller 2.

The tomographic image generator 44 generates tomographic images of the heart by performing an MPR process on the frames of the moving image of the heart acquired by the data receiver 31 (S10). The tomographic images may also be generated from the synthetic volume data that has been generated in step 7. At this moment, for example, tomographic images of the respective sites of the basis, the apex and the papillary muscle are generated.

The controller 2 controls the display 6 to display the image for display that has been generated in step 9 and the tomographic image that has been generated in step 10 (S11). This is the end of the process in a case where it is determined to be 'Y' in step 6.

Next, a process in a case where it is determined to be 'N' in step 6 will now be described. When it is determined that the positions of the heart region and the functional image have not been matched yet in step 6 (S6: N), the image position matching part 41 acquires a coordinate transformation parameter (S21).

The coordinate transformation parameter may be one acquired by the data receiver 31 from the medical image database 300 as described previously, or may be one obtained by the image position matching part 41.

Furthermore, the image position matching part 41 matches the positions of the heart region and the functional image, based on the coordinate transformation parameter (S22). The image position matching part 41 transmits the heart image and the functional image to the synthetic image generator 43 together with the result of the position matching (the association relation of the coordinate values).

The synthetic image generator 43 synthesizes these images to generate synthetic volume data (S7).

The synthetic image generator 43 generates a three-dimensional synthetic image by executing a rendering process on the synthetic volume data (S8).

Furthermore, the display image generator 42 generates an image for display based on the synthetic image (S9).

The tomographic image generator 44 generates tomographic images of the heart based on the moving image of the heart (S10).

The controller 2 controls the display 6 to display the image for display that has been generated in step 9 and the tomographic images that have been generated in step 10 (S11). This is the end of the process in a case where it is determined as 'N' in step 6.

A display mode of an image displayed in step 11 will now be described. FIG. 3 shows one example of the display mode. A screen 6A of the display 6 is provided with a synthetic image display region 61A and a tomographic image display region 61B.

In the synthetic image display region 61A, an image for display G generated in step 9 is displayed. This image for display G is an image formed by synthesizing a heart region (a morphological image) Ga and a functional image Gb. The heart region Ga is an image showing the appearance of the heart viewed from a specified angle of view. The functional image Gb is an image expressing the state of wall motion in display colors and gradation.

The functional image Gb is displayed with a specified transparency, whereby a portion of the heart region Ga located under the functional image Gb can be seen therethrough.

In the tomographic image display region 61B, a tomographic image H1 at the basis of the heart, a tomographic image H2 at the papillary muscle, and a tomographic image H3 at the apex are displayed side by side. These tomographic images H1-H3 are, for example, tomographic images at cross-sections orthogonal to a longitudinal axis (a straight line connecting the basis and the apex) of the heart.

Each of the tomographic images H1-H3 may be a still image in a certain phase (for example, the end diastole of the heart), or may be a moving image.

In the case of displaying a moving image, the tomographic images H1-H3 are generated from the respective frames of the moving image of the heart acquired from the medical image database 300 (the frames may be thinned out). Furthermore, in the case of displaying a moving image, it is desired to display an electrocardiogram or the like representing the phase at the same time.

Furthermore, it is possible to specify a partial region of the functional image at the same cross-section position as each of the tomographic images H1-H3, and display each tomographic image H1 in the same display mode as the partial region. Since each of the tomographic images H1-H3 is generated from the same volume data as the functional image, it is possible to easily associate the positions in both the images.

Consequently, it becomes possible to display a synthesized tomographic image of a functional image showing the state of wall motion of the heart and the tomographic images H1-H3, as in the case of a tomographic image based on synthetic volume data. According to the synthesized tomographic image, it is possible to observe both the morphology of the cross-section of the heart and the state of wall motion at the cross-section.

[Action and Advantageous Effect]

The action and advantageous effect of the medical image processing apparatus 1 will now be described.

As described in detail thus far, the medical image processing apparatus 1 acts so as to acquire a morphological image showing the morphology of the heart of an object and a functional image showing the state of wall motion and display a synthetic image based on the morphological image and the functional image.

According to the medical image processing apparatus 1, it is possible to observe the morphology of a heart in detail by using a morphological image (a heart region), and it is also possible to grasp the state of wall motion in detail with reference to a functional image. Further, since the morphological image and the functional image are synthesized and displayed, it is possible to highly accurately grasp a site with favorable wall motion and a site with unfavorable wall motion in the heart.

Therefore, according to the medical image processing apparatus 1, it becomes possible to accurately diagnose and treat a heart disease. In addition, it is also possible to grasp the distribution of the state of wall motion in the heart at a glance.

It is known that the wall motion of a heart has a closer relationship with the position of a culprit coronary artery than the blood vessel constriction rate in specification of the position of the culprit coronary artery in diagnosis of an ischemic heart disease.

Therefore, according to the medical image processing apparatus 1, it is possible to specify the position of the culprit coronary artery with higher accuracy than conventional.

Moreover, according to the medical image processing apparatus 1, it is possible to extract a morphological image (a heart region) of a heart from volume data, and display a synthetic image of the heart region and a functional image. Therefore, it is possible to observe the morphology of the heart in detail. In particular, it is possible to grasp the state of distribution of coronary arteries in detail. Consequently, it is possible to easily specify the position of the culprit coronary artery.

In the case of using a two-dimensional image (a tomographic image) as a morphological image, it is not necessary to extract a heart region.

Moreover, according to the medical image processing apparatus 1, it is possible to display a tomographic image of a heart together with the synthetic image of the morphological image and the functional image of the heart. Consequently, it is possible to grasp the morphology and motion of the heart wall in detail.

The tomographic images do not need to be obtained at the respective parts of the basis, apex and papillary muscle as cross-sections. For example, it is possible to display a tomographic image of at least one of the parts. In addition, it is also possible to properly display tomographic images at cross-section positions other than the above.

In the operation mode described above, a morphological image and functional image of a heart are acquired in advance, and a synthetic image composed of them is displayed. However, it is possible to configure to display the synthetic image while imaging the morphological image and functional image of the heart.

In this case, there is no need to execute both an examination of specification of the position of a culprit coronary artery and a treatment as in the conventional technique, but rather, it is possible to conduct these in a serial process. For this, it is possible to perform a process, for example, as follows.

First, only a functional image is acquired in advance (may be acquired at the same time as a morphological image). A morphological image is captured while a catheter is being inserted into an object. A synthetic image of the captured morphological image and the functional image is displayed. In this morphological image, the shadow of the catheter is seen. The examiner specifies the position of the culprit coronary artery with reference to the synthetic image, and guides the catheter to the specified position for treatment.

By performing treatment in this process, the period for an examination and the number of examinations are reduced, the number of administrations of a contrast agent is reduced, and the radiation amount is reduced, whereby it is possible to decrease load on a patient.

Second Embodiment

A medical image processing apparatus according to a second embodiment of the present invention acquires a morphological image showing the morphology of a heart and a functional image showing the state of wall motion of the heart, extracts a coronary artery region from the morphological image, and displays a synthetic image of the coronary artery region and the functional image.

Figure 4:
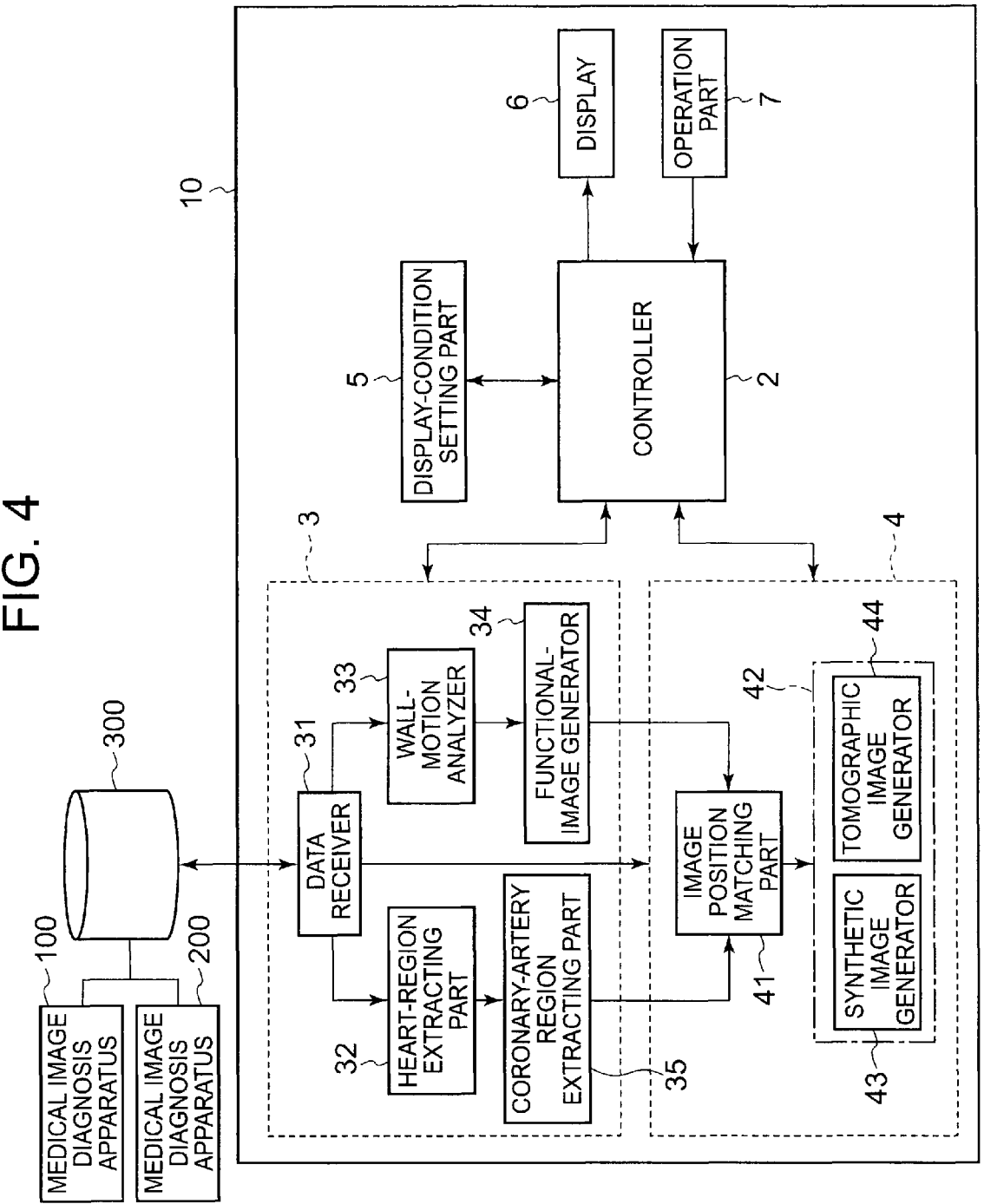
FIG. 4 is a schematic block diagram representing one example of the configuration of a second embodiment of the medical image processing apparatus according to the present invention.

An example of the configuration of the medical image processing apparatus according to the present embodiment is shown in FIG. 4. A medical image processing apparatus 10 comprises a coronary-artery region extracting part 35 included in the data-acquiring part 3, in addition to the configuration of the medical image processing apparatus 1 of the first embodiment (refer to FIG. 1).

The coronary-artery region extracting part 35 extracts a coronary-artery region from the heart region extracted by the heart-region extracting part 32 from the morphological image. The coronary-artery region is an image region corresponding to a coronary artery of a heart in the heart region.

The coronary-artery region extracting part 35 extracts a coronary-artery region by executing threshold processing on the pixel values of pixels composing the heart region. The threshold value is stored beforehand in a hard disk drive or the like. The coronary-artery region extracting part 35 specifically extracts a coronary-artery region from the heart region composed of a three-dimensional image (volume data). The coronary-artery region is a three-dimensional image (volume data).

Furthermore, it is also possible to extract a coronary-artery region by extracting landmarks such as a starting point, a branching point and a tip of a coronary artery and creating a graph (a tree structure) connecting these landmarks.

Instead of automatically extracting the coronary artery region as described above, for example, it is possible to designate the coronary artery region by a dragging operation with a mouse by the operator. The coronary-artery region extracting part 35 extracts the designated region from the image.

The process of extracting the coronary-artery region is not limited to the above, and it is possible to apply any publicly known technology. The coronary-artery region extracting part 35 transmits the extracted coronary-artery region to the image position matching part 41. The coronary-artery region extracting part 35 includes a microprocessor, a RAM, a ROM, a hard disk drive, etc. The coronary-artery region extracting part 35 is one example of the "coronary-artery region extracting part" according to the present invention.

[Operation Mode]

Figure 5:
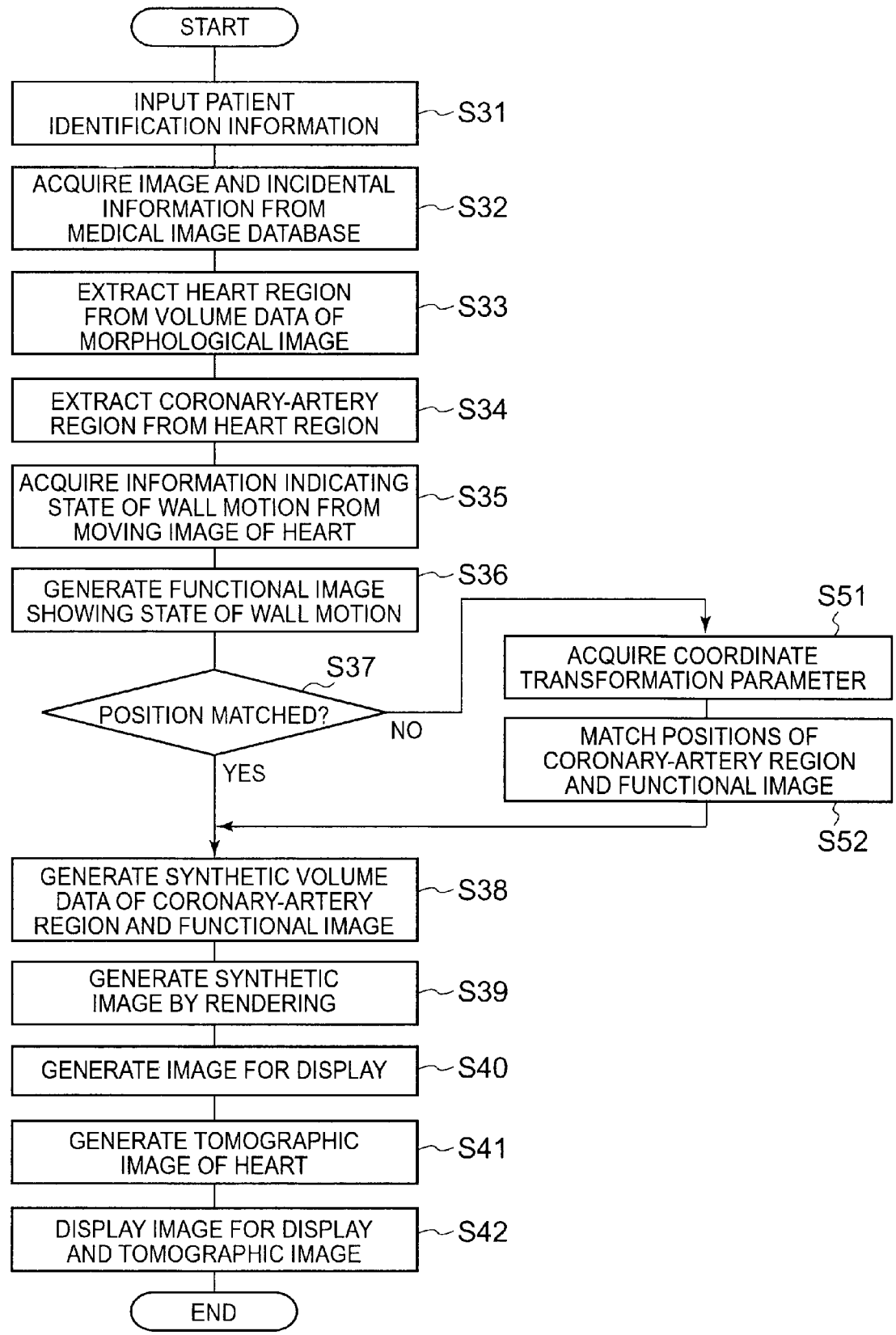
FIG. 5 is a flowchart representing one example of an operation mode of the second embodiment of the medical image processing apparatus according to the present invention.
Figure 6:
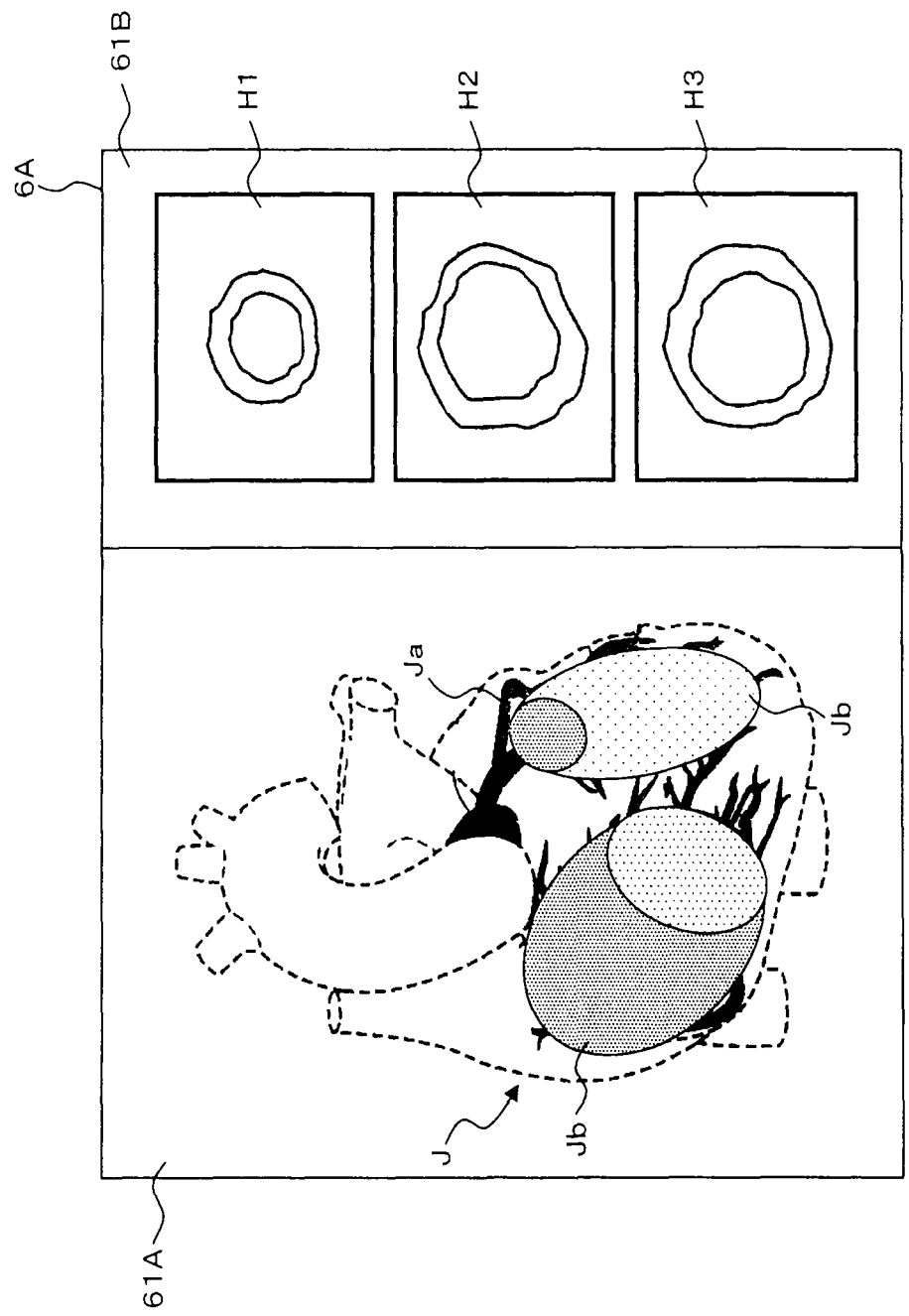
FIG. 6 is a schematic view representing one example of an image displayed in the second embodiment of the medical image processing apparatus according to the present invention.

An operation mode of the medical image processing apparatus 10 will now be described. A flowchart shown in FIG. 5 shows one example of the operation mode of the medical image processing apparatus 10. Furthermore, FIG. 6 shows one example of an image displayed by the medical image processing apparatus 10.

First, the operator inputs patient identification information (S31). The controller 2 transmits the inputted patient identification information to the data-acquiring part 3.

The data receiver 31 acquires data (a morphological image, a functional image, incidental information, etc.) from the medical image database 300 based on the patient identification information (S32). In this operation mode, it is assumed that volume data (and incidental information thereof) of a three-dimensional morphological image of a range that includes the heart of the patient and a three-dimensional moving image (and incidental information thereof) of the heart are received. The data receiver 31 inputs the volume data into the heart-region extracting part 32 and inputs the moving image into the wall-motion analyzer 33.

The heart-region extracting part 32 extracts a heart region from the volume data of the morphological image (S33). The heart-region extracting part 32 transmits the extracted heart region to the coronary-artery region extracting part 35.

The coronary-artery region extracting part 35 extracts a coronary-artery region from the heart region (S34). The coronary-artery region extracting part 35 transmits the extracted coronary-artery region to the image position matching part 41.

Furthermore, the wall-motion analyzer 33 acquires information indicating the state of wall motion of the heart (displacement amount, displacement direction, displacement speed, etc.) based on the moving image of the heart (S35). The wall-motion analyzer 33 transmits the acquired information indicating the state of wall motion to the functional-image generator 34.

The functional-image generator 34 generates a functional image showing the state of wall motion based on the information indicating the state of wall motion (S36). The functional-image generator 34 transmits the generated functional image to the image position matching part 41.

It is possible to execute a process of steps 33 and 34 first, or a process of steps 35 and 36 first. Otherwise, it is possible to execute both the processes in parallel.

The image position matching part 41 determines whether position matching using a landmark, etc., of the heart has already been executed on the coronary-artery region extracted in step 34 and the functional image generated in step 36 (S37). This process is performed by, for example, determining whether the position matching of the volume data that is the basis of the coronary-artery region and the volume data that is the basis of the functional image has already been performed.

If it is determined that the position matching has already been performed (S37: Y), the image position matching part 41 transmits the coronary-artery region and the functional image to the synthetic image generator 43.

The synthetic image generator 43 synthesizes these images (both are volume data) and generates synthetic volume data (S38).

Subsequently, the synthetic image generator 43 generates a three-dimensional synthetic image, which is a pseudo three-dimensional image, by rendering the synthetic volume data (S39).

Furthermore, the display image generator 42 generates an image for display by changing the projection method, angle of view, shift, rotation, etc., of the synthetic image (S40).

The tomographic image generator 44 generates tomographic images of the heart by performing MPR processing or the like on the frames of the moving image of the heart (S41). The tomographic images may be generated from the synthetic volume data that has been generated in step 38. At this moment, for example, a tomographic image at each of the sites of the basis, the apex and the papillary muscle is generated.

The controller 2 controls the display 6 to display the image for display that has been generated in step 40 and the tomographic images that have been generated in step 41 (S42). This is the end of the process in a case in which it is determined as 'Y' in step 37.

Next, the process for a case in which it is determined as "N" in step 37 will now be described. In a case where it is determined that the position matching of the coronary-artery region and the functional image has not been performed yet in step 37 (S37: N), the image position matching part 41 acquires a coordinate transformation parameter (S51). The method of acquiring the coordinate transformation parameter is the same as in the first embodiment.

Furthermore, the image position matching part 41 performs position matching of the coronary-artery region and the functional image based on the coordinate transformation parameter (S52). The image position matching part 41 transmits the coronary-artery image and the functional image to the synthetic image generator 43 together with the result of the position matching (the association relation of the coordinate values).

The synthetic image generator 43 generates synthetic volume data by synthesizing these images (S38).

The synthetic image generator 43 generates a three-dimensional synthetic image by volume rendering on the synthetic volume data (S39).

Furthermore, the display image generator 42 generates an image for display based on the synthetic image (S40).

The tomographic image generator 44 generates tomographic images of the heart based on the moving image of the heart (S41).

The controller 2 controls the display 6 to display the image for display that has been generated in step 40 and the tomographic images that have been generated in step 41 (S42). This is the end of the process in a case in which it is determined as 'N' in step 37.

The display mode of images to be displayed in step 42 will now be described. FIG. 6 shows one example of the display mode. The synthetic image display region 61A and the tomographic image display region 61B are provided in the screen 6A of the display 6 as in the first embodiment.

The image for display G that has been generated in step 40 is displayed in the synthetic image display region 61A. The image for display G is an image obtained by synthesizing a coronary-artery region (a morphological image) Ja and a functional image Jb. The coronary artery region Ja is an image showing the appearance of the coronary-artery region viewed from a specified angle of view. A region indicated by the dashed line in FIG. 6 represents a heart region. In an actual display screen, the heart region does not need to be displayed, or may be displayed in a pale color. The functional image Jb is an image indicating the state of wall motion in display colors or gradation.

The functional image Jb is displayed with a specified transparency, and consequently, a portion of the coronary artery region Ja located under the functional image Jb can be seen therethrough.

As in the first embodiment, the tomographic images H1, H2 and H3 at the basis, papillary muscle and apex of a heart are respectively displayed in the tomographic image display region 61B. The tomographic images H1-H3 may be tomographic images based on the functional image of the heart, or may be tomographic images based on the synthetic volume data.

[Action and Advantageous Effect]

The action and advantageous effect of the medical image processing apparatus 10 will now be described.

As described above in detail, the medical image processing apparatus 10 acts so as to acquire a morphological image (a coronary artery region) showing the morphology of the coronary artery of the heart of an object and a functional image showing the state of wall motion, and display a synthetic image based on the morphological image and the functional image.

According to the medical image processing apparatus 10, the morphology of a coronary artery can be observed in detail by using the morphological image (the coronary artery region), and it is possible to grasp the state of wall motion in detail by referring to the functional image. Furthermore, the morphological image and the functional image are synthesized and displayed, so that it is possible to highly accurately grasp a site with favorable wall motion and a site with unfavorable wall motion in the coronary artery of the heart.

Therefore, according to the medical image processing apparatus 10, it becomes possible to diagnose and treat heart diseases with favorable accuracy. Moreover, it is also possible to grasp the distribution of the state of wall motion at a glance.

Furthermore, according to the medical image processing apparatus 10, it is possible to control not to display the parenchyma of a heart, or display the parenchyma in a pale color, so that the morphology of the coronary artery and the distribution state can be observed particularly in detail. Consequently, for example, it becomes possible to easily specify the position of a culprit coronary artery.

Third Embodiment

A medical image processing apparatus according to a third embodiment of the present invention acquires a morphological image showing the morphology of a heart and a functional image showing the state of wall motion of the heart, extracts a heart region from the morphological image, and displays a synthetic image of the heart region and the functional image. Furthermore, the medical image processing apparatus according to the present embodiment makes it possible to display a tomographic image at a desired cross-sectional position of a heart based on the functional image.

Figure 7:
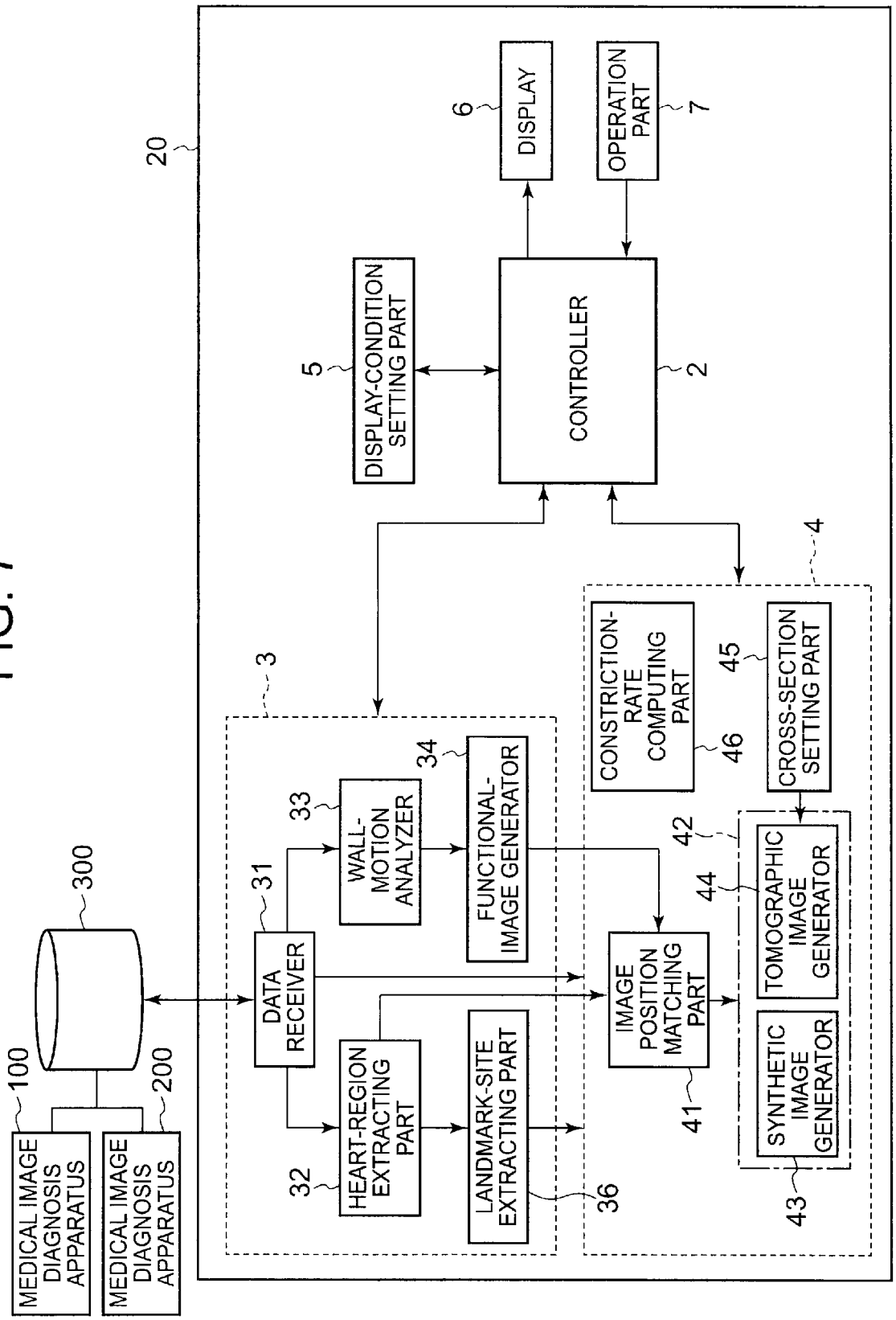
FIG. 7 is a schematic block diagram representing one example of the configuration of a third embodiment according to the medical image processing apparatus according to the present invention.

A configuration example of the medical image processing apparatus according to the present embodiment is shown in FIG. 7. The medical image processing apparatus 20 comprises a landmark-site extracting part 36 included in the data-acquiring part 3, in addition to the configuration of the medical image processing apparatus 1 in the first embodiment (refer to FIG. 1). Furthermore, the data processor 4 of the medical image processing apparatus 20 includes a cross-section setting part 45 and a constriction-rate computing part 46.

The landmark-site extracting part 36 extracts a landmark site of a heart based on the heart region extracted by the heart-region extracting part 32. The landmark site is, for example, the basis, apex, and papillary muscle. The positions in an image corresponding to these sites will be respectively referred to as a basis position, an apex position, and a papillary muscle position. The landmark-site extracting part 36 acts so as to specify the basis position, the apex position, and the papillary muscle position in the heart region.

The process performed by the landmark-site extracting part 36 will now be described. Hereinafter, a process of extracting the basis position and the apex position and a process of extracting the papillary muscle position will be explained separately.

Figure 8:
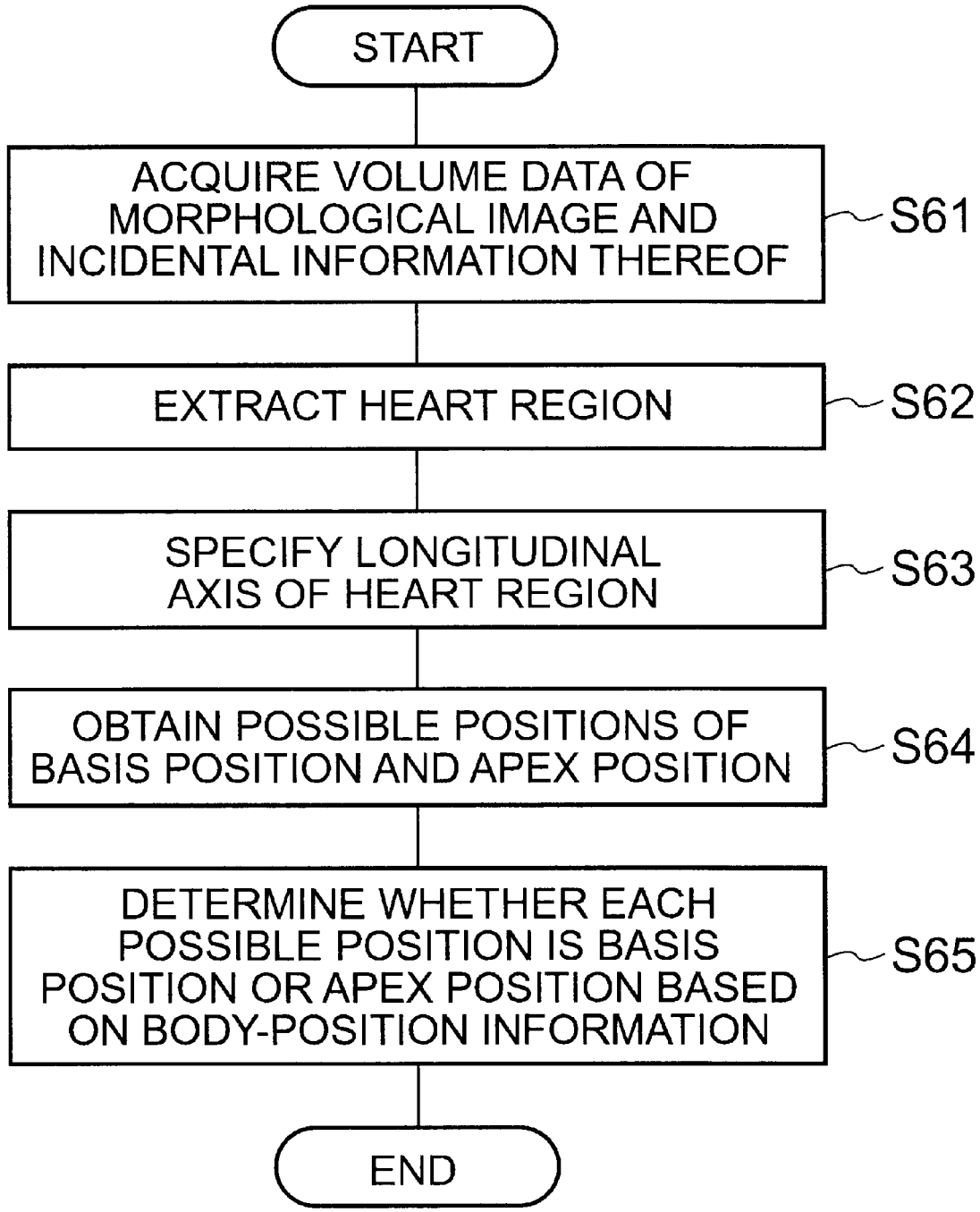
FIG. 8 is a flowchart representing one example of a process executed in the third embodiment of the medical image processing apparatus according to the present invention.

The process of extracting the basis position and the apex position is described with reference to FIG. 8. The flowchart shown in FIG. 8 represents one example of the process.

First, the data receiver 31 acquires volume data of a morphological image and incidental information thereof, and volume data of a functional image and incidental information thereof, from the medical image database 300 (S61). The volume data of the functional image and the incidental information thereof are not subjected to the extraction process of a landmark site.

The incidental information of the morphological image includes body-position information of the morphological image. The body-position information is information indicating the orientation of an object (direction of the head, direction of the lower limb, etc.) in an image, as described above.

Next, the heart-region extracting part 32 extracts a heart region from the volume data of the morphological image (S62).

The landmark-site extracting part 36 specifies the longitudinal axis of the extracted heart region (S63). It is possible to execute this process by, for example, obtaining an ellipsoid similar to the shape of the heart region, obtaining the longitudinal axis of the ellipsoid and defining this as the longitudinal axis of the heart region. Furthermore, it is also possible to extract a border region of the heart region, obtain two points forming the maximum distance on this border region and define a straight line connecting the two points as the longitudinal axis. The process in step 63 can be performed by using any publicly known technology that makes it possible to specify the longitudinal axis of the heart region.

Furthermore, the landmark-site extracting part 36 obtains a possible position of the basis position and a possible position of the apex position in the heart region (S64). This process is performed, for example, as follows.

First, a plane orthogonal to the longitudinal axis of the heart region is obtained. Next, this plane is shifted in the longitudinal direction to search the position on the border region of the heart region that is in contact with the plane. Consequently, two intersection points of the border region with the longitudinal axis of the heart region are specified. Then, these two intersection points are regarded as the possible positions of the basis position and the apex position.

Subsequently, the landmark-site extracting part 36 determines whether each of the possible positions (intersection points) obtained in step 64 is the basis position or the apex position based on the body-position information that has been acquired in step 61 (S65).

As described previously, the body-position information is information indicating the direction of the head or the direction of the lower limb in a morphological image. Furthermore, the longitudinal axis of the heart (the heart region) is inclined with respect to the direction of the body axis of an object, and the inclination angle is not 90 degrees. Therefore, the two possible positions obtained in step 64 exist at different positions in the body-axis direction.

The landmark-site extracting part 36 specifies a position located on the head side and a position located on the lower limb side of the two possible positions. Then, the landmark-site extracting part 36 determines the possible position on the head side as the basis position and the possible position on the lower limb side as the apex position. This is the end of the process of extracting the basis position and the apex position.

Figure 9:
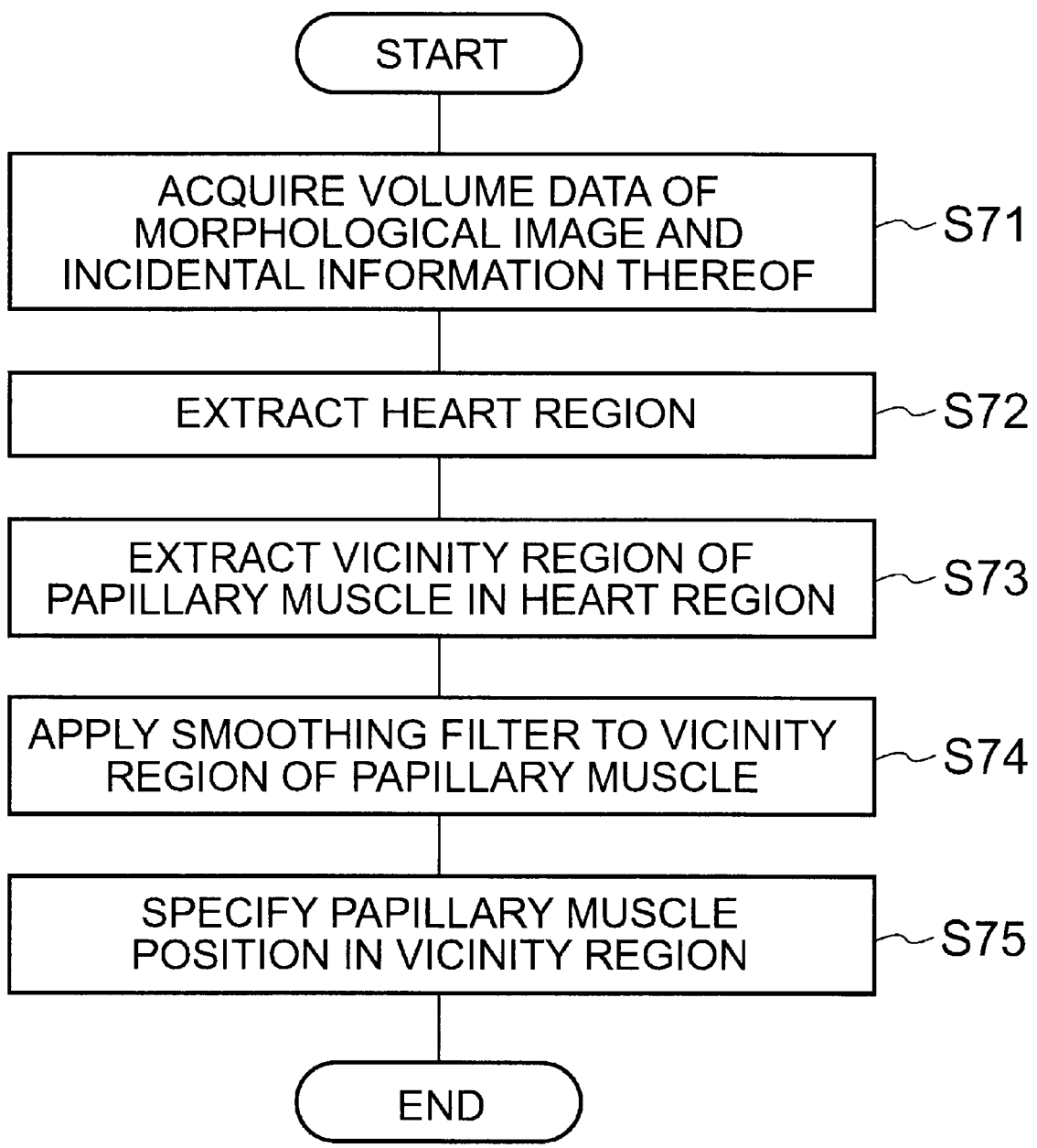
FIG. 9 is a flowchart representing one example of a process executed in the third embodiment of the medical image processing apparatus according to the present invention.

Next, the process of extracting the papillary muscle position is described with reference to FIG. 9. The flowchart shown in FIG. 9 represents one example of the process.

First, the data receiver 31 acquires volume data of a morphological image and incidental information thereof, and volume data of a functional image and incidental information thereof, from the medical image database 300 (S71).

The volume data and the incidental information of the functional image are not subjected to the process of extracting a landmark site. Furthermore, the process in step 71 is the same as the above process of step 61.

Next, the heart-region extracting part 32 extracts a heart region from the volume data of the morphological image (S72). This process is the same as the above process of step 62.

The landmark-site extracting part 36 extracts a vicinity region of the papillary muscle in the heart region (S73). The vicinity region is an image region that includes the papillary muscle position. The process in step 73 is performed, for example, as follows.

The papillary muscle of a heart is composed of three projections: anterior papillary muscle, middle papillary muscle, and posterior papillary muscle. These three papillary muscles are located in a specific range of a heart. The landmark-site extracting part 36 previously stores information indicating the specific range (papillary-muscle range information). The papillary-muscle range information is acquired by, for example, examining the positions of the papillary muscles in the hearts of a large number of objects to obtain a standard position of the papillary muscles in a statistical process on the result of the examination.

The papillary-muscle range information is, for example, a template image formed like the shape of a heart, and information in which a location range of each papillary muscle (a papillary muscle range) in the template image is recorded.

In this case, the landmark-site extracting part 36 first adjusts the size and orientation of the template image about the heart region, and specifies the position in the heart region corresponding to the papillary muscle range. Consequently, the vicinity region of each papillary muscle in the heart region is extracted.

Furthermore, the papillary-muscle range information may be information indicating the position of the papillary muscle with respect to the basis and the apex. The papillary-muscle range information is, for example, information indicating a location range of the papillary muscle on a straight line (a longitudinal axis) connecting the basis and the apex. This information can be acquired by examining the positions of papillary muscles in hearts of a large number of objects.

In this case, the landmark-site extracting part 36 first obtains the longitudinal axis of the heart region as described previously. Next, the landmark-site extracting part 36 specifies a location range of the papillary muscle on the longitudinal axis based on the papillary-muscle range information. Consequently, the vicinity region of each papillary muscle in the heart region is extracted. This ends the explanation of step 73.

Next, the landmark-site extracting part 36 applies a smoothing filter to the vicinity region of the papillary muscle extracted in step 73 (S74).

The smoothing filter is set so as not to erase concaves and convexes that are approximately as large as the radius of curvature of the projection of the papillary muscle, and so as to erase the concaves and convexes that are substantially smaller than the radius of curvature of the papillary muscle.

The respective papillary muscles have distinctive shapes. In particular, the surfaces of the respective papillary muscles have distinctive radii of curvature (curvature). Therefore, a standard value (average, standard deviation, etc.) of the radius of curvature of each papillary muscle can be clinically obtained. The above smoothing filter can be set based on the radius of curvature of each papillary muscle that has been acquired as described above.

By applying this smoothing filter, it is possible to erase small concaves and convexes in the vicinity region of the papillary muscles.

Subsequently, the landmark-site extracting part 36 specifies the position of papillary muscles in the vicinity region to which the smoothing filter has been applied (S75). This process is performed, for example, as follows.

The landmark-site extracting part 36 previously stores the allowable range of the radius of curvature of each papillary muscle (shape information of papillary muscle) based on the standard value of the radius of curvature (curvature) of each papillary muscle that has been clinically acquired as above. The landmark-site extracting part 36 searches a protruding portion having a radius of curvature included in the allowable range, from the vicinity region to which the smoothing filter has been applied, and regards the searched-out protruding portion as a papillary muscle position. This is the end of the process of extracting the papillary muscle position.

[Operation Mode]

Figure 10:
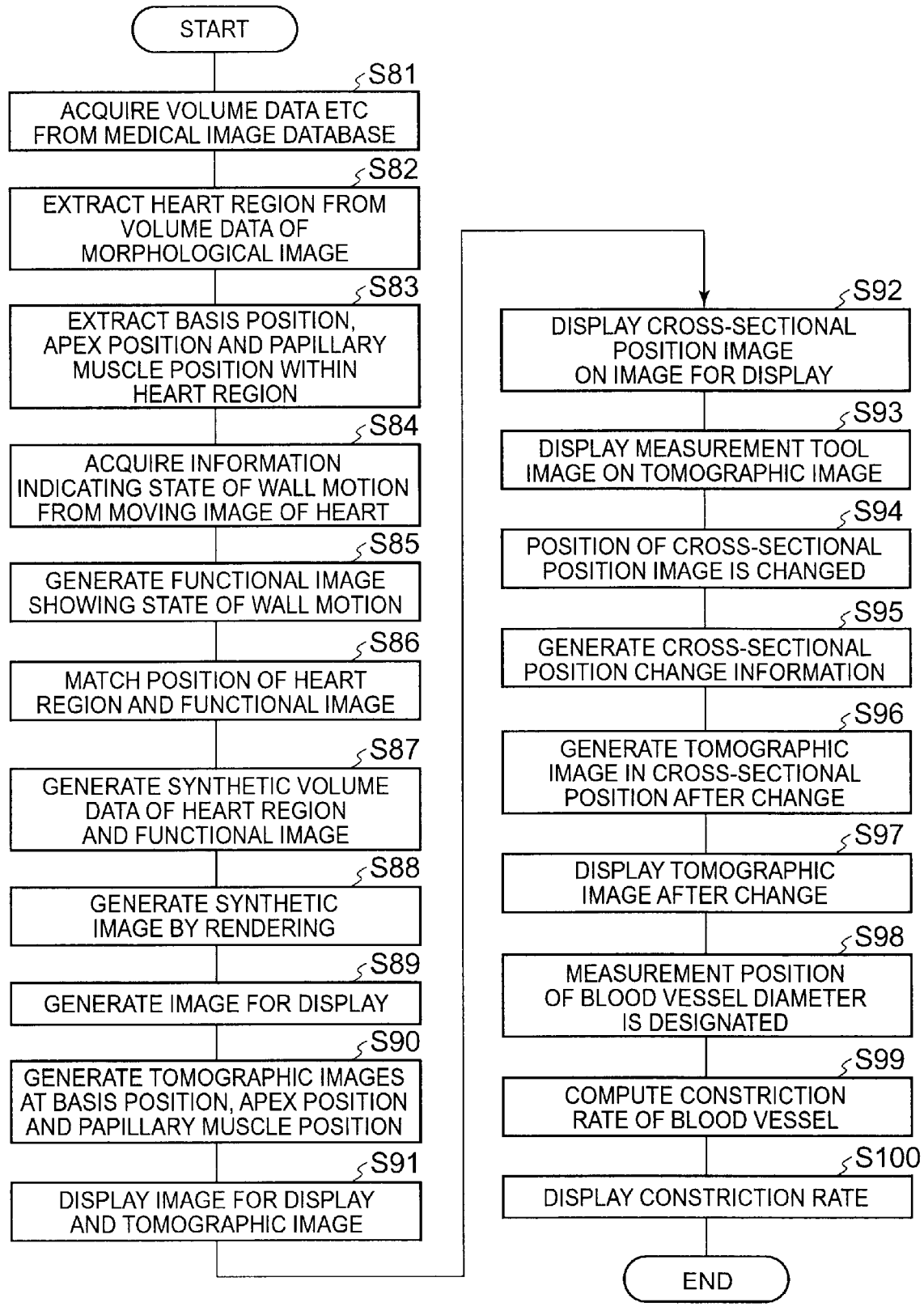
FIG. 10 is a flowchart representing one example of an operation mode of the third embodiment of the medical image processing apparatus according to the present invention.

The operation mode of the medical image processing apparatus 20 according to the present embodiment will now be described. The flowchart shown in FIG. 10 represents one example of the operation modes of the medical image processing apparatus 20.

First, the data receiver 31 acquires the volume data and the incidental information of a morphological image, and the volume data (three-dimensional moving image) and the incidental information of functional information, from the medical image database 300 (S81). This process is the same as the process of the above step 61.

Next, the heart-region extracting part 32 extracts a heart region from the volume data of the morphological image (S82). This process is the same as the process of the above step 62. The extracted heart region is transmitted to the landmark-site extracting part 36 and the image position matching part 41.

The landmark-site extracting part 36 extracts landmark sites within the heart region, i.e., the basis position, the apex position and the papillary muscle position, by following the previously described procedure (S83). The landmark-site extracting part 36 acquires the coordinate value of each landmark site in a three-dimensional coordinate system in which the morphological image has been defined, and transmits to the data processor 4.

Furthermore, the wall-motion analyzer 33 acquires information indicating the state of wall motion of a heart (displacement amount, displacement direction, displacement speed, etc.) based on the three-dimensional moving image (volume data) of the heart (S84). The wall-motion analyzer 33 transmits the acquired information indicating the state of wall motion to the functional-image generator 34.

The functional-image generator 34 generates a functional image showing the state of wall motion based on the information indicating the state of wall motion (S85). The functional-image generator 34 transmits the generated functional image to the image position matching part 41.

It is possible to execute a process of steps 82 and 83 first, or execute a process of steps 84 and 85 first. Otherwise, it is possible to execute these processes in parallel.

As in the first embodiment, the image position matching part 41 matches the positions of the heart region that has been extracted in step 82 and the functional image that has been generated in step 85 (S86). Even if position matching has already been performed, the same process as in the first and second embodiment is executed, but the explanation thereof has been omitted herein.

The synthetic image generator 43 synthesizes the heart region and the functional image (both are volume data) and generates synthetic volume data (S87).

Subsequently, the synthetic image generator 43 renders the synthetic volume data and generates a three-dimensional synthetic image (pseudo three-dimensional image) (S88).

Furthermore, the display image generator 42 generates an image for display by changing the projection method, angle of view, shift, rotation, etc., of the synthetic image (S89).

The tomographic image generator 44 generates tomographic images at the basis position, apex position and papillary muscle position by performing MPR processing on the frames of three-dimensional moving images based on the coordinate values of the basis position, apex position and papillary muscle position that have been acquired in step 83 and based on the results of the position matching of the heart region and the functional image (S90). These tomographic images may be generated from the synthetic volume data that has been generated in step 87.

The controller 2 controls the display 6 to display the image for display that has been generated in step 89 and the three tomographic images that have been generated in step 90 (S91).

The display mode is similar to that of the first embodiment (refer to FIG. 3). That is, the screen 6A of the display 6 is provided with the synthetic image display region 61A in which the image for display is displayed and the tomographic image display region 61B in which the three tomographic images are displayed.

Furthermore, the controller 2 controls to display a cross-sectional position image on the image for display based on the coordinate values acquired in step 83 and the result of the position matching (S92). The cross-sectional position image represents the cross-sectional position of each of the above three tomographic images in the image for display (refer to FIG. 11 described later).

Moreover, the controller 2 controls to display a measurement tool image for measuring the constriction rate of a blood vessel in the tomographic image display region 61B (refer to FIG. 11 described later) (S93).

Figure 11:
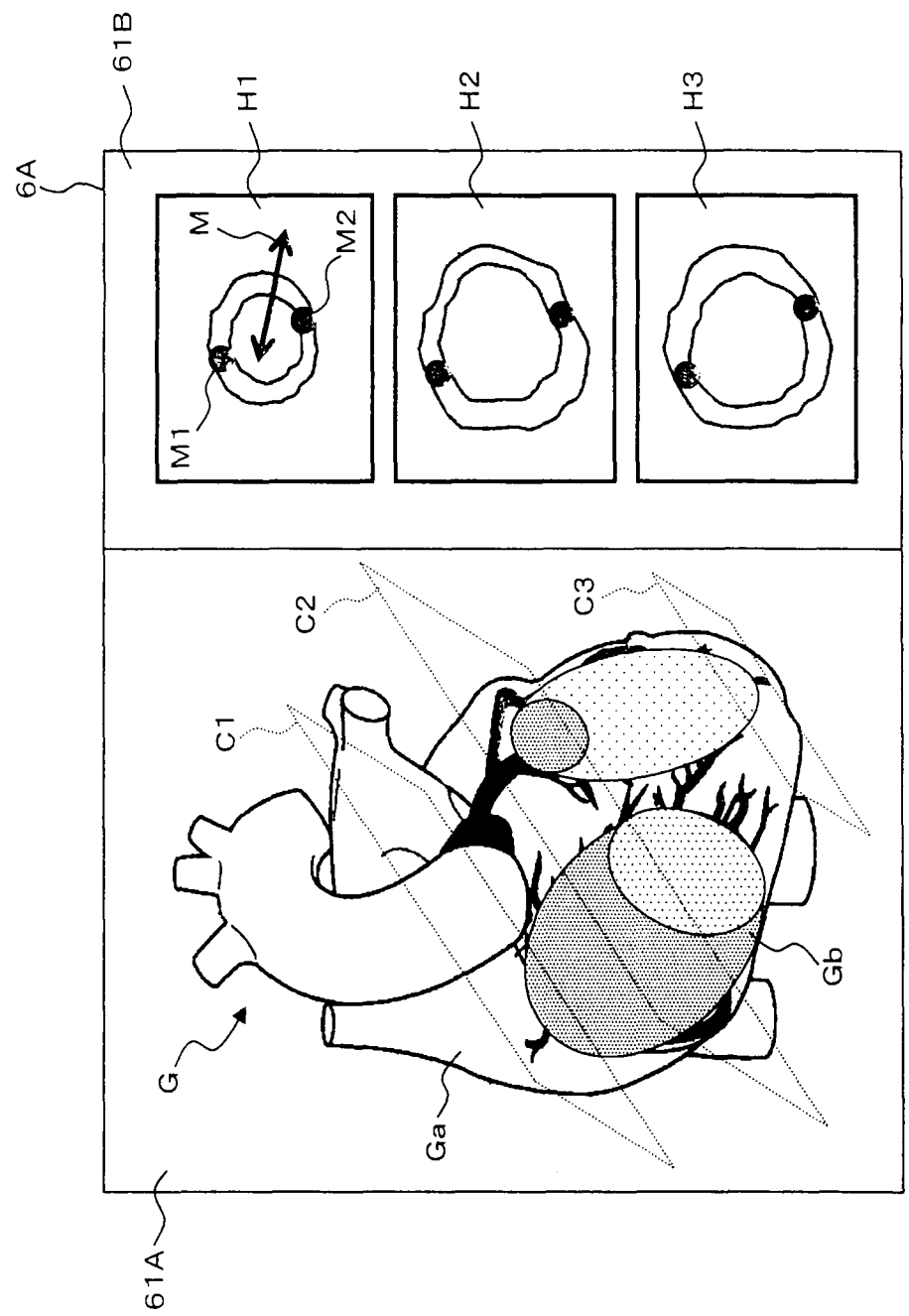
FIG. 11 is a schematic view representing one example of an image displayed in the third embodiment of the medical image processing apparatus according to the present invention.

FIG. 11 shows an example of the mode of an image displayed in the present embodiment. The image for display G is displayed in the synthetic image display region 61A by the process in step 91. The image for display G is an image based on a synthetic image composed of the heart region Ga and the functional image Gb.

Moreover, in the tomographic image display region 61B, the first, second and third tomographic images H1, H2 and H3 are displayed side by side by the process in step 91.

On the image for display G, cross-sectional position images C1, C2 and C3 representing first, second and third cross-sectional positions are displayed by the process in step 92. At the stage of step 92, each of the cross-sectional position images C1-C3 is displayed as a plane orthogonal to the longitudinal axis of the heart region (previously described). Furthermore, at the stage of step 92, the cross-sectional position image C1 is displayed at the basis position, the cross-sectional position image C2 is displayed at the papillary muscle position, and the cross-sectional image C3 is displayed at the apex position.

The cross-sectional position image C1 represents the cross-sectional position (first cross-sectional position) of the first tomographic image H1 in the image for display G. Likewise, the cross-sectional position images C2 and C3 respectively represent the cross-sectional positions (second and third cross-sectional positions) of the second and third tomographic images H2 and H3 in the image for display G.

The operator can change the positions of the respective cross-sectional position images C1-C3, i.e., the cross-sectional positions by using the operation part 7. This operation is performed, for example, via a dragging operation with a mouse. The change of the positions of the cross-sectional position images C1-C3 includes not only parallel shift of the cross-sectional position images C1-C3 but also change in orientation of the cross-sectional position images C1-C3.

When the operator changes the position of a cross-sectional position image Ci (i=1, 2, 3), the controller 2 transmits, to the data processor 4, the coordinate information indicating the position of the cross-sectional position image Ci after the change. The coordinate information is represented by, for example, a coordinate value in a three-dimensional coordinate system defining synthetic volume data.

The cross-section setting part 45 generates information specifying the position (including the orientation) of the cross-sectional position image Ci after the change (cross-sectional position change information) (S95) based on the coordinate information. The cross-section setting part 45 transmits the generated cross-sectional position change information to the tomographic image generator 44.

The cross-sectional position change information includes, for example, the coordinate value representing the position of the cross-sectional position image Ci after the change or the normal direction of a cross-section (indicating the orientation of the cross-section). Furthermore, it is also possible to obtain the equation of a plane formed by the cross-sectional position image Ci to generate the cross-sectional position change information including the equation.

The information is expressed in a three-dimensional coordinate system in which the synthetic volume data has been defined. The three-dimensional coordinate system in which the synthetic volume data has been defined is associated with the three-dimensional coordinate system in which the volume data of the morphological image has been defined and with the three-dimensional coordinate system in which the volume data of the functional image has been defined (cf. the previously described coordinate transformation parameter).

The tomographic image generator 44 generates a tomographic image whose cross-section is a position specified by the cross-sectional position change information (S96). The new tomographic image is acquired by setting, in the volume data of the functional image or the synthetic volume data, a cross-section of the position change and performing an MPR process or the like.

The controller 2 controls to display the new tomographic image generated in step S96, in place of an $i^{th}$ tomographic image Hi before the cross-sectional position change (S97). Consequently, the tomographic image is updated and displayed.

The operator can grasp the position of a culprit coronary artery by observing the image for display G. Furthermore, it is possible to find a constricted site of a coronary artery by observing the image for display G or the tomographic image.

The operator sets a cross-sectional position image Ci at a constricted site or a normal site (a site other than the constricted site) in step 94.

By the process in step 93, a measurement tool image is displayed in the tomographic image display region 61B. A measurement tool image M shown in FIG. 11 is an image having a shape like a both side arrow mark. The operator can shift the measurement tool image M to a site where the operator would like to measure the distance on the tomographic image Hi, and can change the length of the measurement tool image M. This operation is performed, for example, via a dragging operation or the like with a mouse.

Moreover, when the operator designates two positions within the tomographic image Hi, the medical image processing apparatus 20 can obtain the distance between these two positions. The measurement tool images M1 and M2 shown in FIG. 11 represent two positions designated as described above.

The operator can display, for example, the tomographic image of a coronary artery (may be enlarged for display) in the tomographic image display region 61B, and designate the measurement position of the diameter of a blood vessel of the coronary artery at the cross-sectional position by using the measurement tool images M, M1 and M2.

When the operator thus designates the measurement position of the diameter of the blood vessel (S98), the controller 2 transmits the coordinate information indicating the designated position to the data processor 4. The coordinate information is represented, for example, in a coordinate value of a three-dimensional coordinate system in which the synthetic volume data has been defined.

The constriction-rate computing part 46 calculates the constriction rate of the blood vessel based on the coordinate information (S99). The calculating process is performed, for example, as follows.

Herein, the process of a case in which the constriction rate is computed by a method known as the Length method will now be described. According to the Length method, a blood vessel constriction rate SL is obtained by using the following equation.

Formula 1

$$SL\ (\%) = \frac{Ln - Ls}{Ln} \times 100 \quad (1)$$

Herein, Ln denotes the diameter of the blood vessel in a normal site and Ls denotes the diameter of the blood vessel in a constricted site. A higher value of the constriction rate SL means a higher degree of constriction, and SL=100% means complete constriction.

In the case of using the Length method, a measurement position in the normal site and a measurement position in the constricted site are respectively designated in step 98. The coordinate information of the measurement position in the normal site and the coordinate information of the measurement area in the constricted site are entered into the constriction-rate computing part 46.

The constriction-rate computing part 46 computes a blood vessel diameter Ln in the normal site based on the coordinate information of the measurement position in the normal site. Likewise, the constriction-rate computing part 46 computes a blood vessel diameter Ls in the constricted site. Furthermore, the constriction-rate computing part 46 substitutes these two blood vessel diameters Ln and Ls into the above formula (1), thereby computing a vasoconstriction rate SL in the constricted site.

The controller 2 controls the display 6 to display the computed vasoconstriction rate SL (S100). This ends the explanation of the operation mode.

The constriction-rate computing part 46 is one example of the "computing part" according to the present invention.

[Action and Advantageous Effect]

The actions and advantageous effect of the medical image processing apparatus 20 according to the present embodiment will now be described.

As in the medical image processing apparatus 1 in the first embodiment, the medical image processing apparatus 20 acts so as to acquire a morphological image (heart region) showing the morphology of the heart of an object and a functional image showing the state of wall motion, and display a synthetic image based on the morphological image and the functional image, so that it is possible to diagnose and treat heart diseases with accuracy. Furthermore, the distribution of the state of wall motion in a heart can be grasped at a glance.

Moreover, the medical image processing apparatus 20 acts so as to automatically specify a landmark site of a heart region and display a tomographic image of the heart at the landmark site. Therefore, by previously setting landmark sites frequently referred to, such as the basis position, the apex position and the papillary muscle position, it is possible to easily observe the tomographic image of the landmark site without manually designating the landmark site.

Furthermore, in response to a change made by the operator regarding the position of a cross-sectional position image on an image for display, the medical image processing apparatus 20 acts so as to automatically generate and display a tomographic image for a cross-section of the post-change state. Consequently, the operator can easily observe the tomographic image at a desired cross-sectional position.

Moreover, the medical image processing apparatus 20 acts so as to automatically compute the constriction rate of a blood vessel at a measurement position in response to the designation of the measurement position within a tomographic image by the operator by using the measurement tool image. Consequently, it is possible to measure the vasoconstriction rate via a simple operation.

Fourth Embodiment

As in the second embodiment, a medical image processing apparatus according to the fourth embodiment according to the present invention displays a synthetic image of a coronary artery region and a functional image, and also displays an appearance image showing the appearance of a heart.

Only from the synthetic image of the coronary artery region and the functional image, it is difficult to grasp, for example, which orientation a coronary artery region is displayed in. Furthermore, when focusing on a specific site of the coronary artery region, it is difficult to grasp the position of the specific site in the heart. This embodiment is for solving such an inconvenience by displaying an appearance image.

Figure 12:
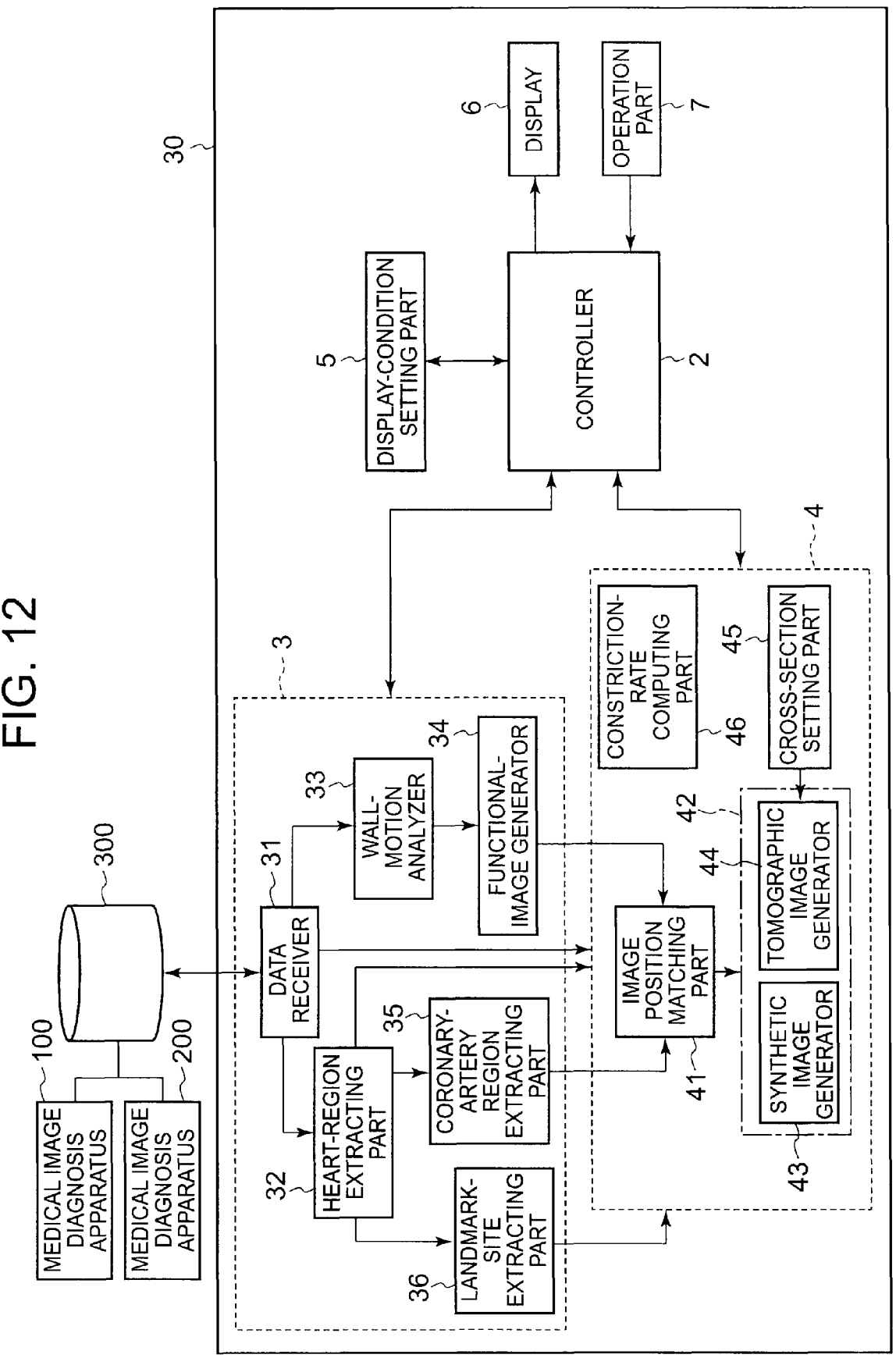
FIG. 12 is a schematic block diagram representing one example of the configuration of a fourth embodiment according to the medical image processing apparatus according to the present invention.

A configuration example of the medical image processing apparatus according to the present embodiment is shown in FIG. 12. A medical image processing apparatus 30 comprises a coronary-artery region extracting part 35 similar to that of the second embodiment, in addition to the configuration of the medical image processing apparatus 20 of the third embodiment (refer to FIG. 7).

[Operation Mode]

Figure 13:
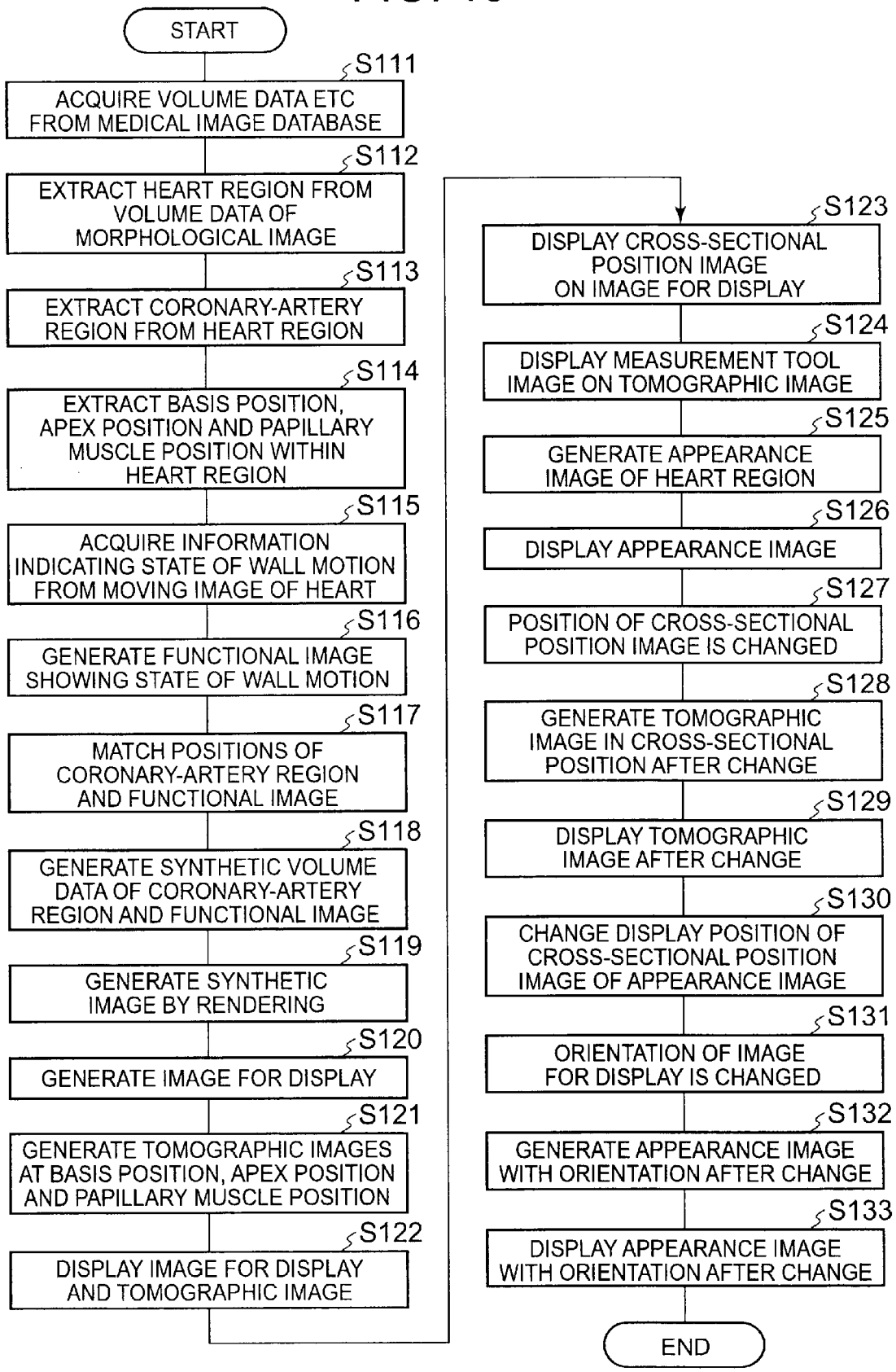
FIG. 13 is a flowchart representing one example of an operation mode in the fourth embodiment of the medical image processing apparatus according to the present invention.

The operation mode of the medical image processing apparatus 30 will now be described. A flowchart shown in FIG. 13 shows one example of the operation mode of the medical image processing apparatus 30.

First, the data receiver 31 acquires volume data of a morphological image and incidental information thereof, and volume data (three-dimensional moving image) of functional information and incidental information thereof, from the medical image database 300 (S111).

Next, the heart-region extracting part 32 extracts a heart region from the volume data of the morphological image (S112). This process is the same as step 62 described above. The extracted heart region is transmitted to the coronary-artery region extracting part 35, the landmark-site extracting part 36, and the data processor 4.

The coronary-artery region extracting part 35 extracts a coronary-artery region from the heart region (S113). The coronary-artery region extracting part 35 transmits the extracted coronary-artery region to the image position matching part 41.

The landmark-site extracting part 36 extracts landmark sites, such as the basis position, the apex position and the papillary muscle position, in the heart region (S114). The landmark-site extracting part 36 acquires the coordinate value of each of the landmark sites in a three-dimensional coordinate system in which the morphological image is defined, and transmits it to the data processor 4.

Moreover, the wall-motion analyzer 33 acquires information indicating the state of wall motion of a heart based on a three-dimensional moving image (volume data) of the heart (S115). The wall-motion analyzer 33 transmits the acquired information to the functional-image generator 34.

The functional-image generator 34 generates a functional image showing the state of wall motion based on the information indicating the state of wall motion (S116). The functional-image generator 34 transmits the generated functional image to the image position matching part 41.

It is possible to first execute any process of steps 112 and 113, the process of step 114, or the process of steps 115 and 116. Otherwise, these processes may be executed in parallel.

The image position matching part 41 matches the position of the coronary artery region extracted in step 113 and the position of the functional image generated in step 116 (S117).

The synthetic image generator 43 synthesizes the coronary-artery region and the functional image (both are volume data) to generate synthetic volume data (S118).

Subsequently, the synthetic image generator 43 generates a three-dimensional synthetic image (a pseudo three-dimensional image) by executing a rendering process on the synthetic volume data (S119).

Furthermore, the display image generator 42 changes the projection method, angle of view, shift, rotation, etc., of the synthetic image and generates an image for display (S120).

The tomographic image generator 44 executes an MPR process on the frames of the three-dimensional moving image, based on the coordinate values of the landmark sites obtained in step 114 and the result of the position matching of the coronary artery region and the functional image, thereby generating tomographic images at the basis position, the apex position and the papillary muscle position, respectively (S121). These tomographic images may be generated from the synthetic volume data generated in step 118.

The controller 2 controls the display 6 to display the image for display generated in step 120 and the three tomographic images generated in step 90 (S122).

Furthermore, as in the third embodiment, the controller 2 controls to display a cross-sectional position image on the image for display (S123) and display a measurement tool image on the tomographic image (S124).

Moreover, the display image generator 42 generates an appearance image (a pseudo three-dimensional image) of the heart region based on the heart region (volume data) extracted in step 112 (S125). As with the synthetic image generator 43, this process can be performed by rendering the volume data of the heart region and generating the image for display when required. The controller 2 controls the display 6 to display the appearance image (S126).

Figure 14:
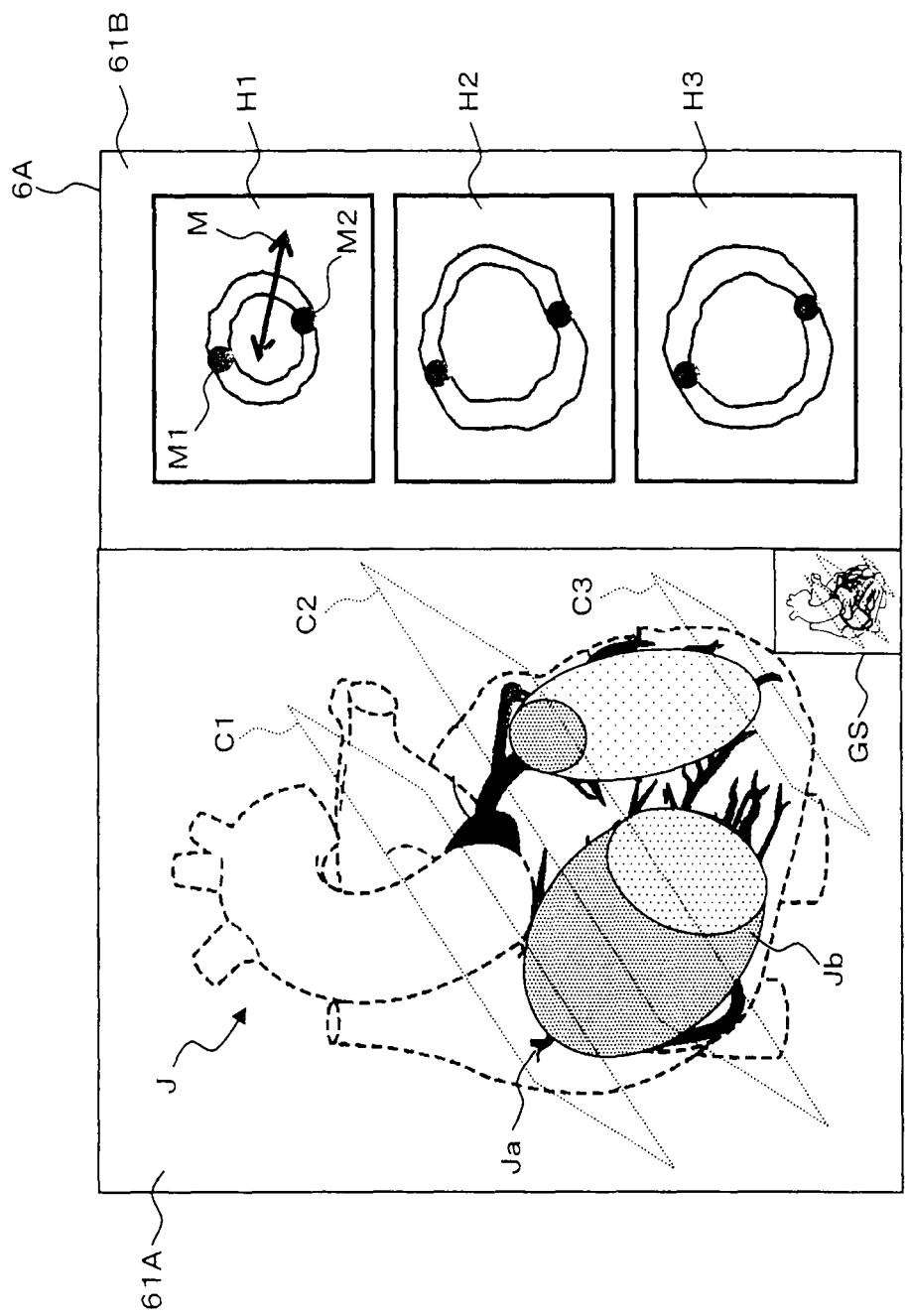
FIG. 14 is a schematic view representing one example of an image displayed in the fourth embodiment of the medical image processing apparatus according to the present invention.

FIG. 14 shows an example of the mode of an image displayed in the present embodiment. In a synthetic image display region 61A, an image for display J is displayed by the process of step 122. The image for display J is an image based on a synthetic image of a coronary-artery region Ja and a functional image Jb. In the present embodiment, only the coronary-artery region Ja is displayed, and the actual portion of the heart (dashed-line portion in this figure) is not displayed.

Moreover, in a tomographic image display region 61B, the first, second and third tomographic images H1, H2 and H3 are displayed side by side by the process of step 122.

On the image for display J, the cross-sectional position images C1, C2 and C3 are displayed by the process of step 123. Furthermore, on the tomographic image Hi (i=1, 2, 3), the measurement tool image M is displayed by the process of step 124. Moreover, when the operator designates a measurement position, the controller 2 controls to display measurement tool images M1 and M2 on the tomographic image Hi.

Furthermore, in a synthetic image display region 61A, an appearance image GS is displayed by the process of step 126. The appearance image GS is, for example, a thumbnail of the pseudo three-dimensional image of the heart region. In this case, a thumbnail generating process is executed in the image-for-display generating process of step S125. The appearance image GS is not limited to a thumbnail. However, the appearance image GS is for grasping the orientation, etc., of the image for display J, and a major observation object is the image for display J, so that it is preferable that the appearance image GS is small in size so as not to restrict the display size of the image for display J.

Furthermore, the appearance image GS in FIG. 14 includes a cross-sectional position image showing the cross-sectional position of the tomographic image Hi.

When the operator changes the position of a cross-sectional position image Ci (i=1, 2, 3) (S127), the controller 2 generates cross-sectional position change information for specifying the position of the cross-sectional position image Ci after the change, based on the coordinate information of the cross-sectional position image Ci after the change. The tomographic image generator 44 generates a tomographic image at a cross-section specified by the cross-sectional position change information (S128). The controller 2 controls to display the new tomographic image (S129).

Furthermore, the display image generator 42 changes the display position of the cross-sectional position image of the appearance image GS based on the coordinate information of the cross-sectional position image Ci after the change (S130). This process can be easily performed by using the association between the coordinate system of the synthetic volume data that is the basis of the image for display J and the coordinate system of the volume data that is the basis of the appearance image GS (volume data of a heart image).

Furthermore, when the operator changes the orientation of the image for display J by using the operation part 7 (S131), the controller 2 transmits information indicating the orientation after the change to the data processor 4. Based on the information, the display image generator 42 generates an appearance image after the orientation is changed (S132). This process is acquired by rendering the volume data of the heart region, taking the orientation after the change as the angle of view. The controller 2 controls to display the new appearance image in place of the appearance image GS before the orientation is changed (S133).

Since the computation of the constriction rate of a coronary artery is similar to that in the third embodiment, an explanation thereof is omitted. This is the end of the explanation of the operation mode.

[Action and Advantageous Effect]

The action and advantageous effect of the medical image processing apparatus 30 according to the present embodiment will now be described.

The medical image processing apparatus 30 acts so as to display an appearance image of a heart together with a synthetic image composed of a coronary artery region and a functional image. Furthermore, the medical image processing apparatus 30 changes the orientation of the appearance image of the heart, in response to change of the orientation of the synthetic image. Consequently, it becomes possible to easily grasp the orientation of the synthetic image and the position of the coronary-artery region in the heart region.

Moreover, according to the medical image processing apparatus 30, a cross-sectional position image showing the cross-sectional position of a tomographic image displayed together with the synthetic image is displayed in the state attached to the appearance image of the heart. Furthermore, according to the medical image processing apparatus 30, in response to change of the position of the cross-sectional position image on the synthetic image, the position of the cross-sectional position image on the appearance image is also changed. Consequently, it is possible to easily and accurately grasp the location of the cross-sectional position of the tomographic image in the heart region.

[Modification]

The embodiments described in detail thus far are merely examples for implementing the medical image processing apparatus according to the present invention. Therefore, it is possible to apply any modification within the scope of the present invention.

In the third embodiment, the operator designates the position to measure a vasoconstriction rate in a cross-sectional image, but the operation is not restricted to the above. For example, it is possible to automate measurement of a vasoconstriction rate, by executing a process as described below (in the case of employing the Length method):
(1) extract a coronary-artery region from a heart region; (2) specify a constricted site and a normal site in this coronary-artery region; (3) set a cross-sectional position corresponding to each of the constricted site and the normal site; (4) generate a tomographic image of a heart at each of the cross-sectional positions; (5) specify a cross-sectional region of the coronary artery in each of the tomographic images; (6) obtain the diameter of each of the cross-sectional regions; and (7) compute the constriction rate based on the diameter value of the cross-section region of the constricted site and the diameter value of the cross-section region of the normal site.

The process (1) can be executed as in the second embodiment. The process (2) can be executed in such a way as described below. A threshold value of a feature quantity (e.g., a CT value in the case of an X-ray CT apparatus) of the constricted site is previously set. The data processor 4 can specify the constricted site and the normal site by executing threshold processing on the voxel value of voxels forming a coronary-artery region.

In the process (3), it is possible to set a cross-sectional position corresponding to the constricted site, by obtaining a plane passing through the specified constricted site (e.g., a plane orthogonal to the longitudinal axis of a heart region). The same applies to the normal site.

The process (4) can be executed by obtaining a cross-sectional position in a functional image based on the association between the coordinate system of a synthetic image (an image for display) and the coordinate system of a functional image and generating a tomographic image at the cross-section by MPR processing or the like. The process (5) can be executed by specifying a position within the tomographic image, which corresponds to the position (coordinate value) of the coronary artery region extracted in (1).

The process (6) can be executed, for example, by obtaining the maximum diameter of the cross-section region. The process (7) can be executed as in the third embodiment.

According to this modification, it is possible to easily obtain the vasoconstriction rate. Any one of the above processes (1)-(7) may manually be performed. For example, it is possible to configure to manually perform the processes (2), (3), (5), etc.

In the above embodiments, the explanation has been given for a case in which the morphological image and the functional image are both three-dimensional image (volume data), but at least one of these may be a two-dimensional image (tomographic image).

In a case where the morphological image is a two-dimensional image, for example, in a case where the morphological image is a two-dimensional tomographic image (a tomographic morphological image), there is no need to execute the process of extracting a heart region and a coronary-artery region. That is, in a case where the morphological image is a three-dimensional image, there is a case where it is impossible to visually recognize the heart region, etc., due to an image of a body site existing around the heart (e.g., a rib), so that it is desired to extract the heart region or the like. On the other hand, in a case where the morphological image is a two-dimensional image, it is possible to visually recognize the cross section of the heart region, etc., as far as the cross section passes through the heart region, etc., so that it is not required to extract the heart region, etc.

Furthermore, in a case where the functional image is a two-dimensional moving image, it is possible to acquire the state of wall motion based on the two-dimensional image as conventional. Moreover, in a case where the functional image is a two-dimensional image, it is impossible to display a tomographic image of another cross-section. In a case where tomographic images at a plurality of cross-sections have been acquired, there is a case where it is possible to generate volume data by interpolating between adjacent tomographic images. In this case, it is possible to generate a new tomographic image at a new cross-section.

Even in the case of using a two-dimensional image as the morphological image or the functional image, it is possible to specify the approximate position of a culprit coronary artery, and it is possible to use for catheter treatment or the like.

In the above embodiments, a moving image is used as the functional image, and this is for obtaining the state of wall motion of a heart. Therefore, in a case where a still image of the heart (a three-dimensional image or tomographic image) and information indicating the state of wall motion of the heart (wall motion information) are stored in the medical image database 300, it is possible to use the still image and the wall motion information as the functional image.

According to the medical image processing apparatus according to the above embodiment, it is possible to specify a culprit coronary artery with ease and with high accuracy by observing the synthetic image. It is possible to provide a part configured to mark (designate) the culprit coronary artery having been thus designated. As this part, for example, it is possible to employ the operation part 7 (mouse). The position of the marked culprit coronary artery is obtained as a coordinate value of the coordinate system of the synthetic image or synthetic volume data. It is desired to store the coordinate value in a hard disk drive or in the medical image database 300. The stored information is, for example, retrieved at the time of treatment and used as information indicating the position of the culprit coronary artery (e.g., present the position in an image at the time of medical treatment). Consequently, it is possible to facilitate the catheter treatment.

Furthermore, when an image region corresponding to the culprit coronary artery (a culprit coronary artery region) is designated on the synthetic image, it is possible to clarify the region within a tomographic image that corresponds to the culprit coronary artery region. This treatment is executed by the data processor 4, for example, in the following manner.

It is assumed that a synthetic image and a tomographic image are displayed on the display 6. First, the operator designates a culprit coronary artery region on the synthetic image by using the operation part 7. The data processor 4 specifies a region (a blood vessel region) within a three-dimensional functional image corresponding to the culprit coronary artery region. This process can be performed by referring to the association between the coordinate system of the synthetic image and the coordinate system of the functional image.

Next, the data processor 4 specifies a common region of the blood vessel region and the tomographic image by referring to the association of the coordinate systems. The common region corresponds to the cross-section of the culprit coronary artery in the tomographic image. The controller 2 controls to display information indicating the common region on the tomographic image. This information is, for example, a display color, gradation etc. Furthermore, it is also possible to display an image surrounding the common region.

According to the modification, it is possible to easily grasp which position in the tomographic image the culprit coronary artery region designated on the synthetic image exists in.

In the above embodiment, the morphological image and the functional image are acquired by receiving the three-dimensional image and the three-dimensional moving image of the object from outside, but it is not limited to the above description.

For example, it is possible to configure the medical image processing apparatus to receive tomographic images at a plurality of cross-sectional positions of an object from outside the apparatus, generate a three-dimensional image (volume data) based on the plurality of tomographic images, and acquire a morphological image based on the three-dimensional image. At this moment, the three-dimensional moving image that is the basis of the functional image is received from outside the apparatus.

Likewise, it is also possible to configure the medial image processing apparatus to receive tomographic images (moving image) at a plurality of cross-sectional positions of an object, generate a three-dimensional moving image (volume data) based on the plurality of tomographic images, and acquire a functional image based on the three-dimensional moving image. At this moment, the three-dimensional image to become the basis of the morphological image is received from outside the apparatus.

Furthermore, it is possible to configure to receive both the plurality of tomographic images to become the basis of a morphological image and the plurality of tomographic images (tomographic moving image) to become the basis of the functional image, from outside the apparatus. In this case, the medical image processing apparatus generates a three-dimensional image (volume data) based on the plurality of tomographic images having been received and acquires the morphological image based on the three-dimensional image. Moreover, the medical image processing apparatus generates a three-dimensional moving image (volume data) based on the plurality of received tomographic images and generates a functional image based on the three-dimensional moving image.

In the above embodiments, the method of observing a synthetic image and specifying a culprit coronary artery has been described in detail. However, it is also possible to configure to automatically specify the (possible) culprit coronary artery. It is possible to perform the process, for example, based on the relative positional relation between the branch of a coronary artery and a site with abnormal wall motion. Below, four examples of this process will be described.

In recent years, technology for specifying the anatomical position of a branch of a coronary artery has been developed (e.g., cf. http://www.inria.fr/chir). In a first example, a site with abnormal wall motion is first specified by analyzing a functional image. Next, the branch within the coronary artery region corresponding to the anatomical position of the abnormal site is specified. This specified branch is regarded as a possible culprit coronary artery. The possible coronary artery is displayed in a mode that is recognizable in a synthetic image.

As a second example, it is possible to specify a possible culprit coronary artery based on the result of the simulation of myocardial infarction. The simulation of myocardial infarction is described, for example, in the *Journal of the Institute of Electronics, Information and Communication Engineers* D-II Vol. J88-D-II No. 5 pp. 943-953, Institute of Electronics, Information and Communication Engineers 2005 (http://www.bme.sys.i.kyoto-u.ac.jp/~amano/publications/j88-d2_5_943.pdf).

In a third example, first, the abnormal site regarding wall motion is specified by analyzing a functional image. Furthermore, by consecutively enlarging the abnormal site with the use of a morphological filter, the first branch crossing the enlarged region is regarded as a culprit coronary artery. The morphological filter is technology that is conventionally used widely in the field of image processing. Moreover, in addition to the first branch that has crossed the enlarged region, it is also possible to appropriately regard other branches crossing the enlarged region as possible culprit coronary arteries.

In a fourth example, first, the abnormal site associated wall motion is specified by analyzing a functional image. Moreover, the distance from the branch of the coronary artery region to the abnormal site is calculated, and a branch wherein the calculated distance falls within a specified threshold value is regarded as a possible culprit coronary artery.

As described above, it becomes possible to make the work of specifying a culprit coronary artery more effective and to enable effort saving by automatically specifying the possible culprit coronary artery. That is, the work of specifying a possible culprit coronary artery may be made easier or time can be saved by automatically narrowing down the possible culprit coronary arteries.

As described above, the medical image processing apparatus according to the present invention acts so as to acquire a morphological image and a functional image of a heart to display a synthetic image based on these images, and specify a culprit coronary artery region within the synthetic image based on the functional image to display information indicating the specified culprit coronary artery region together with the synthetic image. Consequently, it is possible to increase the accuracy of diagnosis and treatment.

Moreover, as described in the above embodiments, the medical image processing apparatus according to the present invention is capable of generating a tomographic image of a heart based on a morphological image, specifying a common region of the tomographic image and a culprit coronary artery region, and display information indicating the common region on the tomographic image. Consequently, it is possible to refer to the tomographic image as well as a synthetic image, and it becomes possible to further enhance the accuracy of a diagnosis and a treatment.

In the above embodiments, an examination of a heart has been described in detail, but it is also possible to implement the same examination for organs other than heart as long as the organ allows the acquisition of both morphological image and functional image. For example, by employing a method called perfusion of acquiring data in which bloodstream dynamics is incorporated, it is possible to form a functional image for not only a heart but also for organs such as brain, liver, gallbladder, pancreas, etc., by employing. As in the above embodiment, it is possible to display a synthetic image of the morphological image and the functional image. The perfusion has been disclosed in, e.g., Japanese Unexamined Patent Application Publication No. H6-269424. Moreover, the image to be processed in this modification may be a three-dimensional image or may also be a two-dimensional image.

The medical image processing apparatus related to the modification comprising an acquiring part for acquiring a morphological image showing the morphology of an organ of an object as well as a functional image showing the state of the organ, which has been formed by different medical image diagnosis apparatuses and display, is constituted so as to display a synthetic image based on the morphological image as well as the functional image.

Functional images are divided into the following two types: (1) images acquired by detecting data in which the function of an organ is incorporated and by imaging the detected results of the data; (2) images acquired by analyzing a morphological image that is formed by detecting data in which the morphology of an organ is incorporated. The functional state of an organ is measured and imaged in the functional image of (1). As for the method of forming functional images in (1), for example, there are: nuclear medical diagnosis (PET, SPECT, etc.), or spectroscopy as well as diffusion imaging by an MRI apparatus. The functional state of an organ such as movement is imaged in the functional images in (2) by analyzing morphological images (particularly a moving image). As for the method of forming functional images in (2), for example, there are: an image of bloodstream speed image in contract photographing, perfusion, functional MRI (f-MRI).

According to the medical image processing apparatus related to the modification, the morphology of an organ may be observed in detail by a morphological image and it is also possible to grasp the state of the organ in detail by using a functional image as reference. Furthermore, because the morphological image and the functional image may be synthesized and displayed, it is possible to grasp, with high accuracy, which area of an organ is functioning favorably or unfavorably. Therefore, it becomes possible to make a diagnosis or the treatment of the organ with favorable accuracy.

[The Medical Image Diagnosis Apparatus]

The medical image diagnosis apparatus according to the present invention will now be described. From here on, three embodiments shown in FIGS. 15-17 will now be described. It should be noted that only a medical image diagnosis apparatus having a configuration in compliance with the first embodiment is described, but it is also possible to apply a configuration in compliance with the second to the fourth embodiment as well as the above modification.

The medical image diagnosis apparatus according to the present invention is X-ray diagnosis apparatus, X-ray CT apparatus, MRI apparatus, ultrasound diagnosis apparatus, nuclear medical diagnosis apparatus, or the combination of these apparatuses (e.g., PET-CT, SPECT-CT, etc.).

Figure 15:
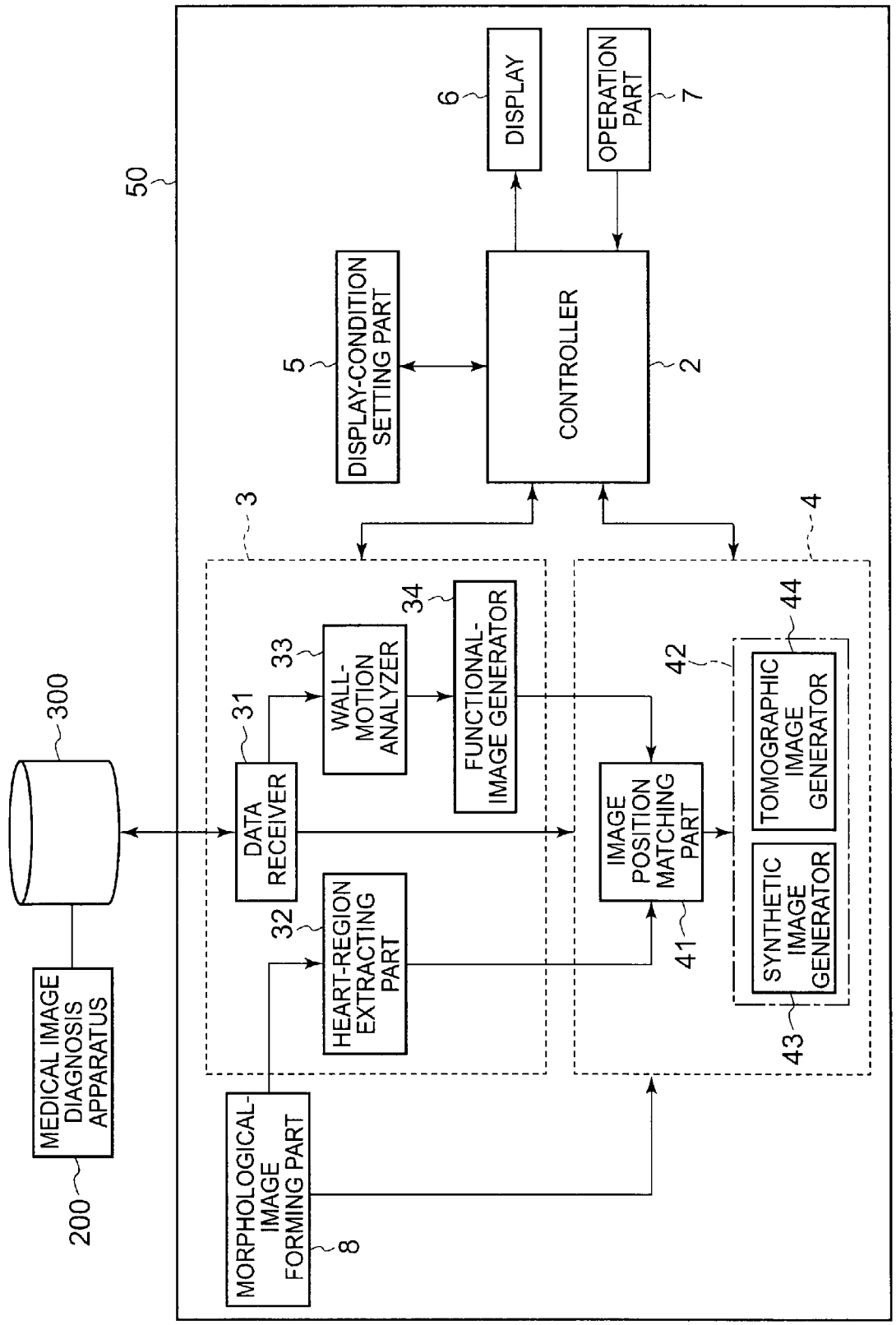
FIG. 15 is a schematic block diagram representing one example of the configuration of an embodiment of the medical image diagnosis apparatus according to the present invention.

The medical image diagnosis apparatus 50 shown in FIG. 15 comprises a morphological-image forming part 8. The morphological-image forming part 8 detects data in which the morphology within an object is incorporated, and forms a morphological image showing the morphology of a range that includes the heart of the object based on the data. The morphological-image forming part 8 is one example of the "morphological-image forming part" according to the present invention.

For example, if the medical image diagnosis apparatus 50 is an X-ray CT apparatus, the morphological-image forming part 8 includes a gantry, bed, reconstruction board, etc. The gantry has an X-ray tube and an X-ray detector that have been disposed oppositely to each other. Furthermore, the gantry is provided with a rotation mechanism for integrally rotating the X-ray tube and the X-ray detector. Moreover, the gantry is provided with a DAS (data acquisition system) for collecting data detected by the X-ray detector. The DAS transmits the collected data to the reconstruction board. The reconstruction board executes preprocessing for converting the data from the DAS to projection data or reconstituting process for reconstituting an image based on the projection data.

The image formed by the morphological-image forming part 8 (morphological image) is transmitted to the heart-region extracting part 32.

On the other hand, a functional image is formed by a medical image diagnosis apparatus 200 as in the first embodiment, and is stored in the medical image database 300. The data receiver 31 of the medical image diagnosis apparatus 50 acquires the functional image and the incidental information from the medical image database 300.

The following process is the same as in the first embodiment.

According to the medical image diagnosis apparatus 50, the morphology of a heart may be observed in detail by a morphological image and it is possible to grasp the state of wall motion in detail by using a functional image as reference. Furthermore, because the morphological image and the functional image are synthesized and displayed, it is possible to grasp, with high accuracy, the wall motion of which area of a heart is favorable or unfavorable.

Therefore, according to the medical image diagnosis apparatus 50, it becomes possible to diagnose or treat heart disease with favorable accuracy. Furthermore, the distribution of the state of wall motion in a heart may be grasped at a glance.

Figure 16:
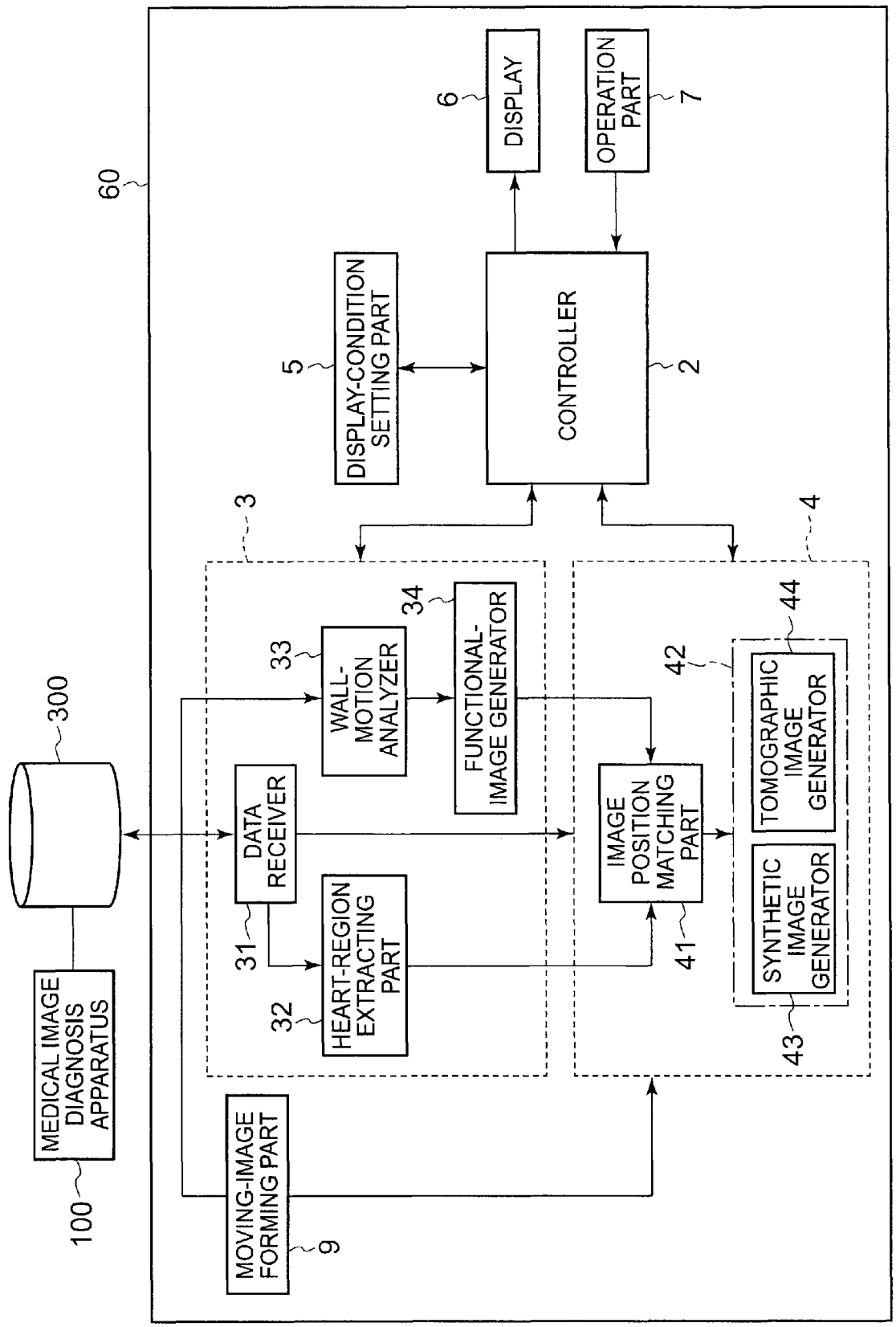
FIG. 16 is a schematic block diagram representing one example of the configuration of the embodiment of the medical image diagnosis apparatus according to the present invention.

The medical image diagnosis apparatus 60 shown in FIG. 16 comprises a moving image-forming part 9. The moving image-forming part 9 detects data in which the morphology within an object is incorporated, and forms a moving image of a range that includes the heart of the object based on the data.

The moving image-forming part 9 is one example of the "moving image-forming means" according to the present invention.

For example, if the medical image diagnosis apparatus 60 is an ultrasound diagnosis apparatus, the moving image-forming part 9 is constituted so as to include an ultrasound probe, ultrasound-transmitting/receiving board, signal processing board, image processing board, etc. The ultrasound probe is controlled by the ultrasound-transmitting/receiving board and transmits/receives ultrasound beams in a specified scan mode. The signal processing board generates various types of ultrasound images such as B-mode image, Doppler image, and CFM (Color flow matching) image based on the reception results of the ultrasound beams. The image processing board has a DSC (digital scan converter). The DSC converts data that has been generated by the signal processing board and has been synchronized with ultrasound scan to display data (such as data of television scanning system). Furthermore, the image processing board generates volume data by subjecting a multiple number of B-mode images to interpolation process.

The moving image (volume data, etc.) generated by the moving image-forming part 9 is transmitted to the wall-motion analyzer 33.

On the other hand, morphological images are formed by the medical image diagnosis apparatus 100 as in the first embodiment, and are stored in the medical image database 300. The data receiver 31 of the medical image diagnosis apparatus 60 acquires the morphological images and the incidental information from the medical image database 300.

The subsequent process is the same as in the first embodiment.

According to the medical image diagnosis apparatus 60, as in the above medical image diagnosis apparatus 50, it becomes possible to diagnose or treat heart disease with favorable accuracy, and the distribution of the state of wall motion in a heart may be grasped at a glance.

Figure 17:
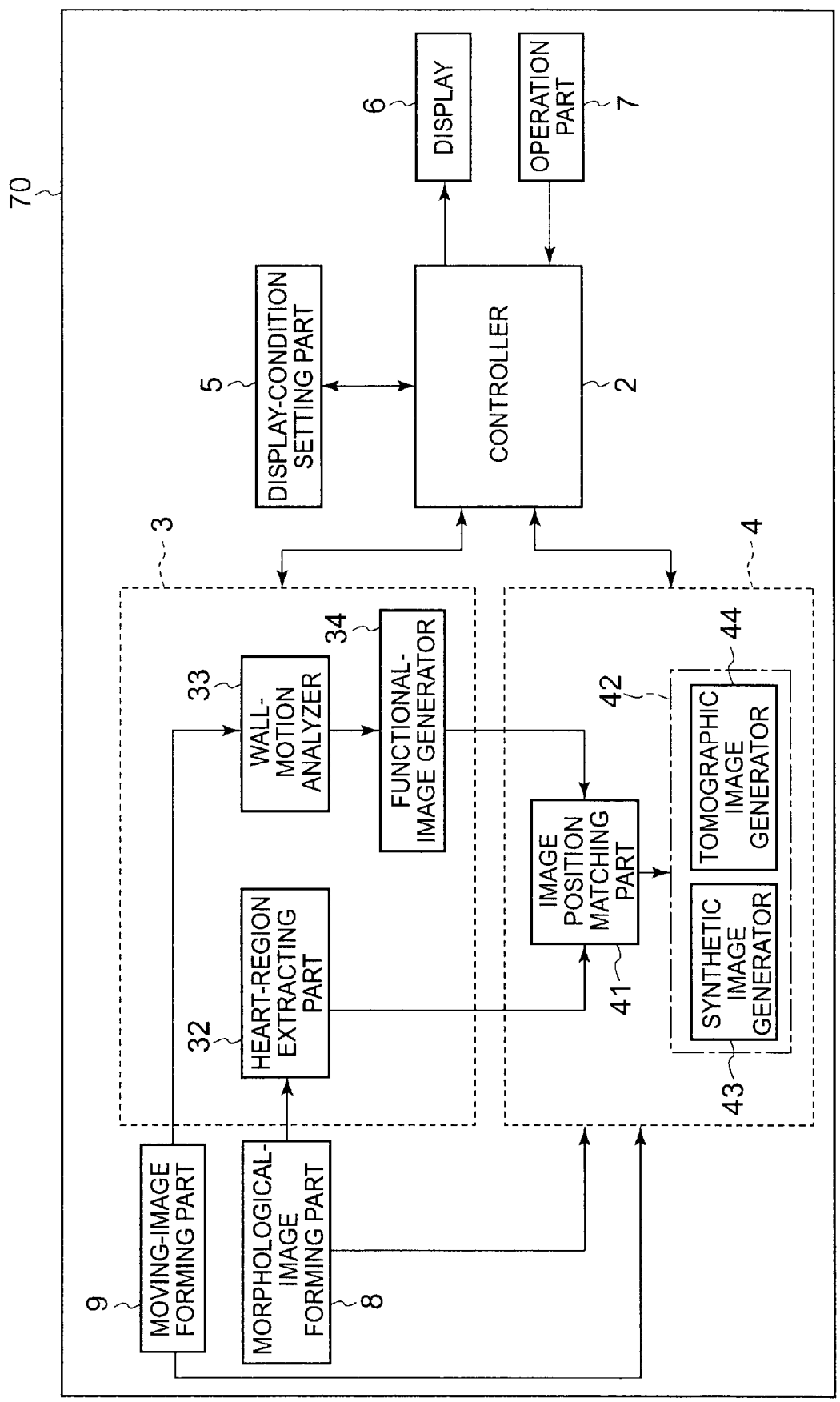
FIG. 17 is a schematic block diagram representing one example of the configuration of the embodiment of the medical image diagnosis apparatus according to the present invention.

The medical image diagnosis apparatus 70 shown in FIG. 17 comprises both the morphological-image forming part 8 and the moving-image forming part 9. The medical image diagnosis apparatus 70 does not need to be connected to the medical image database 300 or the other medical image diagnosis apparatuses. Therefore, the medical image diagnosis apparatus 70 does not need to have the data receiver 31.

According to the medical image diagnosis apparatus 60, as in the above medical image diagnosis apparatuses 50 and 60, it is possible to diagnose or treat heart disease with favorable accuracy and the distribution of the state of wall motion in a heart may be grasped at a glance.

If the medical image diagnosis apparatus according to the present invention is an apparatus capable of forming morphological images, the medical image diagnosis apparatus includes a part configured to form morphological images (morphological-image forming part), a part configured to receive functional images from outside, a display, and a processor.

As in the above embodiments, the morphological-image forming part detects data in which the morphology within an object is incorporated, and forms a morphological image showing the morphology of a range that includes an organ of the object based on the detected data.

The part configured to receive functional images receives a functional image that has been formed by other medical image diagnosis apparatuses and represents the state of the organ. For example, if the medical image diagnosis apparatus is an X-ray CT apparatus, the X-ray CT apparatus receives a functional image of a heart that has been formed by an ultrasound diagnosis apparatus. This functional image may be directly inputted from the ultrasound diagnosis apparatus, and may also be inputted via a storage device such as PACS or via a recording media (DVD-R, etc.).

The processor causes the display to display a synthetic image based on the formed morphological image and the received functional image.

According to such a medical image diagnosis apparatus, the morphology of an organ may be observed in detail by a morphological image and it is also possible to grasp the state of the organ in detail by using the functional image as reference. Furthermore, because the morphological image and the functional image may be synthesized and displayed, it is possible to grasp, with high accuracy, the part of an organ that is functioning favorably or unfavorably. Therefore, it becomes possible to make a diagnosis and the treatment of the organ with favorable accuracy.

On the contrary, if the medical image diagnosis apparatus according to the present invention is an apparatus capable of forming functional images, the medical image diagnosis apparatus includes a part configured to form functional images, a part configured to receive morphological images from outside, a display, and a processor.

As in the above embodiments, the part configured to form functional images detects data in which the function or the morphology of an organ is incorporated, and forms a functional image showing a state of the organ based on the detected data. As the method of forming functional images by detecting data that indicates the function of an organ, for example, there are: Doppler ultrasound diagnosis, nuclear medical diagnosis (PET, SPECT, etc.), spectroscopy or diffusion by an MRI apparatus. On the other hand, as the method of forming functional images by detecting data that indicates the morphology of an organ, for example, there are: image of blood stream speed by contrast photographing, perfusion, and functional MRI.

The part configured to receive morphological images receives a morphological image showing the morphology of the organ formed by another medical image diagnosis apparatus. For example, if the medical image diagnosis apparatus is an ultrasound diagnosis apparatus, the ultrasound diagnosis apparatus receives a morphological image of a heart formed by an X-ray CT apparatus. The morphological image may be directly inputted from the X-ray CT apparatus, may be inputted via a storage device such as PACS, or may be inputted via a recording media.

The processor causes the display to display a synthetic image based on the received morphological image and the formed functional image.

According to such a medical image diagnosis apparatus, it is possible to observe in detail the morphology of an organ by a morphological image, and it is possible to grasp the state of the organ in detail by referring to a functional image. Further, because it is possible to synthesize and display the morphological image and the functional image, it is possible to grasp, with high accuracy, a site functioning favorably and a site functioning unfavorably in an organ. Therefore, it becomes possible to accurately diagnose and treat the organ.

Further, the medical image diagnosis apparatus according to the present invention is used for processing of images of a heart, and may also comprise a processor as described below, together with a morphological-image forming part, a functional-image receiving part and a display as described above. That is, the processor causes the display to display a synthetic image based on a morphological image and a functional image, specifies a culprit coronary artery region within the synthetic image based on the functional image, and causes to display information indicating the specified culprit coronary artery region together with the synthetic image.

According to such a medical image diagnosis apparatus, it is possible to increase the accuracy of diagnosis and treatment of a heart. In particular, by making it possible to automatically specify a possible culprit coronary artery, it becomes possible to increase the efficiency and save labor in an operation of specifying a culprit coronary artery.

Further, the medical image diagnosis apparatus according to the present invention is for processing images of a heart, and may also comprise a processor as described below, together with a morphological-image receiving part, a functional-image forming part and a display as described above. That is, the processor causes the display to display a synthetic image based on a morphological image and a functional image, specifies a culprit coronary artery region within the synthetic image based on the functional image, and causes to display information indicating the specified culprit coronary artery region together with the synthetic image.

According to such a medical image diagnosis apparatus, it is possible to increase the accuracy of diagnosis and treatment of a heart. In particular, by making it possible to automatically specify a possible culprit coronary artery, it becomes possible to increase the efficiency and save labor in an operation of specifying a culprit coronary artery

What is claimed is:

1. A medical image diagnosis apparatus comprising:
   a morphological-image forming part configured to detect data in which a morphology of the inside of an object is incorporated and form a morphological image showing a morphology of a range including an organ of the object based on the detected data;
   a part configured to receive an analysis image formed by another medical image diagnosis apparatus and representing a state of the organ;
   a wall motion analyzer configured to analyze the analysis image to determine a state of wall motion of the organ;
   a functional image generator configured to generate a functional image reflecting the state of wall motion determined by the wall motion analyzer;
   a display; and
   a processor configured to cause the display to display a synthetic image based on the morphological image and the functional image.

2. A medical image diagnosis apparatus comprising:
   a part configured to receive a morphological image formed by another medical image diagnosis apparatus and representing a morphology of a range including an organ of an object;
   a part configured to detect data in which a function or morphology of the organ is incorporated and form an analysis image showing a state of the organ based on the detected data;
   a wall motion analyzer configured to analyze the analysis image to determine a state of wall motion of the organ;
   a functional image generator configured to generate a functional image reflecting the state of wall motion determined by the wall motion analyzer;
   a display; and
   a processor configured to cause the display to display a synthetic image based on the morphological image and the functional image.

3. A medical image diagnosis apparatus comprising:
   a morphological-image forming part configured to detect data in which a morphology of the inside of an object is incorporated and form a morphological image showing the morphology of a range including a heart of the object based on the detected data;
   a part configured to receive an analysis image formed by another medical image diagnosis apparatus and representing a state of wall motion of the heart;
   a wall motion analyzer configured to analyze the analysis image to determine the state of wall motion of the heart;
   a functional image generator configured to generate a functional image reflecting the state of wall motion determined by the wall motion analyzer;
   a display; and
   a processor configured to cause the display to display a synthetic image based on the morphological image and the functional image, specify a culprit coronary artery region in the synthetic image based on the functional image, and display information indicating the specified culprit coronary artery region together with the synthetic image.

4. A medical image diagnosis apparatus comprising:
   a part configured to receive a morphological image formed by another medical image diagnosis apparatus and representing a morphology of a range including a heart of an object;
   a part configured to detect data indicating a function or morphology of the heart and form an analysis image showing a state of wall motion of the heart based on the detected data;
   a wall motion analyzer configured to analyze the analysis image to determine the state of wall motion of the heart;
   a functional image generator configured to generate a functional image reflecting the state of wall motion determined by the wall motion analyzer;
   a display; and
   a processor configured to cause the display to display a synthetic image based on the morphological image and the functional image, specify a culprit coronary artery region in the synthetic image based on the functional image, and cause to display information indicating the specified culprit coronary artery region together with the synthetic image.

5. A medical image diagnosis apparatus comprising:
   a morphological-image forming part configured to detect data in which a morphology of the inside of an object is incorporated and form a morphological image showing a morphology of a range including an organ of the object based on the detected data;
   a part configured to receive a functional image formed by another medical image diagnosis apparatus and representing a state of the organ;
   a display; and
   a processor configured to cause the display to display a synthetic image based on the morphological image and the functional image, wherein the functional image is volume data and the processor is configured to generate synthetic volume data from the functional image and apply rendering processing on the synthetic volume data to generate the synthetic image.

6. A medical image diagnosis apparatus comprising:
   a part configured to receive a morphological image formed by another medical image diagnosis apparatus and representing a morphology of a range including an organ of an object;
   a part configured to detect data in which a function or morphology of the organ is incorporated and form a functional image showing a state of the organ based on the detected data;

a display; and a processor configured to cause the display to display a synthetic image based on the morphological image and the functional image, wherein the functional image is volume data and the processor is configured to generate synthetic volume data from the functional image and apply rendering processing on the synthetic volume data to generate the synthetic image.

7. A medical image diagnosis apparatus comprising:

a morphological-image forming part configured to detect data in which a morphology of the inside of an object is incorporated and form a morphological image showing the morphology of a range including a heart of the object based on the detected data;

a part configured to receive a functional image formed by another medical image diagnosis apparatus and representing a state of wall motion of the heart;

a display; and a processor configured to cause the display to display a synthetic image based on the morphological image and the functional image, specify a culprit coronary artery region in the synthetic image based on the functional image, and display information indicating the specified culprit coronary artery region together with the synthetic image, wherein the functional image is volume data and the processor is configured to generate synthetic volume data from the functional image and apply rendering processing on the synthetic volume data to generate the synthetic image.

8. A medical image diagnosis apparatus comprising:

a part configured to receive a morphological image formed by another medical image diagnosis apparatus and representing a morphology of a range including a heart of an object;

a part configured to detect data indicating a function or morphology of the heart and form a functional image showing a state of wall motion of the heart based on the detected data;

a display; and a processor configured to cause the display to display a synthetic image based on the morphological image and the functional image, specify a culprit coronary artery region in the synthetic image based on the functional image, and cause to display information indicating the specified culprit coronary artery region together with the synthetic image, wherein the functional image is volume data and the processor is configured to generate synthetic volume data from the functional image and apply rendering processing on the synthetic volume data to generate the synthetic image.

* * * * *